(12) United States Patent
Jones et al.

(10) Patent No.: US 12,167,861 B2
(45) Date of Patent: Dec. 17, 2024

(54) TENDON HARVESTING SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Dean Jones, Liberty Hill, TX (US); Paul Alexander Torrie, Marblehead, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 874 days.

(21) Appl. No.: 17/282,953

(22) PCT Filed: Oct. 3, 2019

(86) PCT No.: PCT/US2019/054486
§ 371 (c)(1),
(2) Date: Apr. 5, 2021

(87) PCT Pub. No.: WO2020/072766
PCT Pub. Date: Apr. 9, 2020

(65) Prior Publication Data
US 2021/0386436 A1     Dec. 16, 2021

Related U.S. Application Data

(60) Provisional application No. 62/741,964, filed on Oct. 5, 2018.

(51) Int. Cl.
*A61B 17/17* (2006.01)

(52) U.S. Cl.
CPC ............................ *A61B 17/1764* (2013.01)

(58) Field of Classification Search
CPC .............. A61B 17/1635; A61B 17/158; A61B 17/1677; A61B 17/1714; A61B 17/1764
See application file for complete search history.

(56) References Cited

U.S. PATENT DOCUMENTS

| | | | |
|---|---|---|---|
| 5,021,055 A * | 6/1991 | Burkinshaw | ......... A61B 17/158 |
| | | | 606/88 |
| 5,192,321 A | 3/1993 | Strokon | |
| (Continued) | | | |

FOREIGN PATENT DOCUMENTS

| | | | |
|---|---|---|---|
| DE | 8903079 | 5/1989 | |
| DE | 8903079 U1 | 5/1989 | ............. A61B 17/28 |
| (Continued) | | | |

OTHER PUBLICATIONS

Japanese Application No. 2021-518755 Notice of Reasons for Rejection, dated Aug. 2, 2023.
(Continued)

*Primary Examiner* — Matthew J Lawson
(74) *Attorney, Agent, or Firm* — Norman F. Hainer, Jr.

(57) ABSTRACT

A system for improving graft harvesting including a tendon harvesting instrument for producing a graft from a tendon. The instrument includes a handle, a shaft and a blade portion operatively coupled to the shaft. The blade portion defines a cutting edge that at least partially corresponds to the shape of a graft cross section of the graft. The blade portion is inserted into the tendon by axially rotating the instrument shaft. The blade portion may include a free end for piercing the tendon as the blade portion is rotated into the tendon. The harvesting instrument may also include amputating means for removing the end connection of the graft to the tendon, the amputating means including a means of changing an orientation of an end portion of the cutting edge.

20 Claims, 43 Drawing Sheets

(56) References Cited

U.S. PATENT DOCUMENTS

| | | |
|---|---|---|
| 5,728,118 A | 3/1998 | Dross et al. |
| 5,733,289 A * | 3/1998 | Seedhom .......... A61B 17/1677 606/80 |
| 6,702,813 B1 | 3/2004 | Baxter et al. .......... A61B 18/12 |
| 2004/0158255 A1* | 8/2004 | Justin .................. A61B 17/157 606/87 |
| 2010/0069944 A1 | 3/2010 | Murakami et al. .... A61B 17/32 |
| 2010/0222781 A1* | 9/2010 | Collazo ................ A61F 2/3877 606/89 |
| 2012/0283793 A1 | 11/2012 | Burroughs, III |
| 2013/0211411 A1* | 8/2013 | Tuke .................... A61B 17/157 606/88 |
| 2013/0282009 A1 | 10/2013 | Knodel |
| 2014/0277020 A1 | 9/2014 | Koogle et al. |
| 2014/0358148 A1* | 12/2014 | Olgiati ................ A61B 17/158 606/87 |
| 2015/0190154 A1* | 7/2015 | Rolston ............. A61B 17/1764 606/88 |
| 2016/0066929 A1 | 3/2016 | Russo et al. |
| 2016/0081710 A1 | 3/2016 | Barnes et al. |
| 2016/0270771 A1 | 9/2016 | Hsiao et al. |
| 2018/0014821 A1 | 1/2018 | Weber et al. |

FOREIGN PATENT DOCUMENTS

| | | | |
|---|---|---|---|
| DE | 102011109715 | 5/2019 | |
| EP | 0470903 A1 | 2/1992 | ............. A61B 17/32 |
| FR | 2824467 | 11/2015 | |
| JP | 2010284479 A | 12/2010 | ............... A61F 2/38 |
| WO | WO9816162 | 4/1998 | |
| WO | WO06075909 A | 6/2008 | |

OTHER PUBLICATIONS

Chinese Search Report—Application No. 201980065769.2—dated Sep. 22, 2023.

Search Report and WO for PCT/US2019/054486 dated Feb. 13, 2020, 16 pages.

* cited by examiner

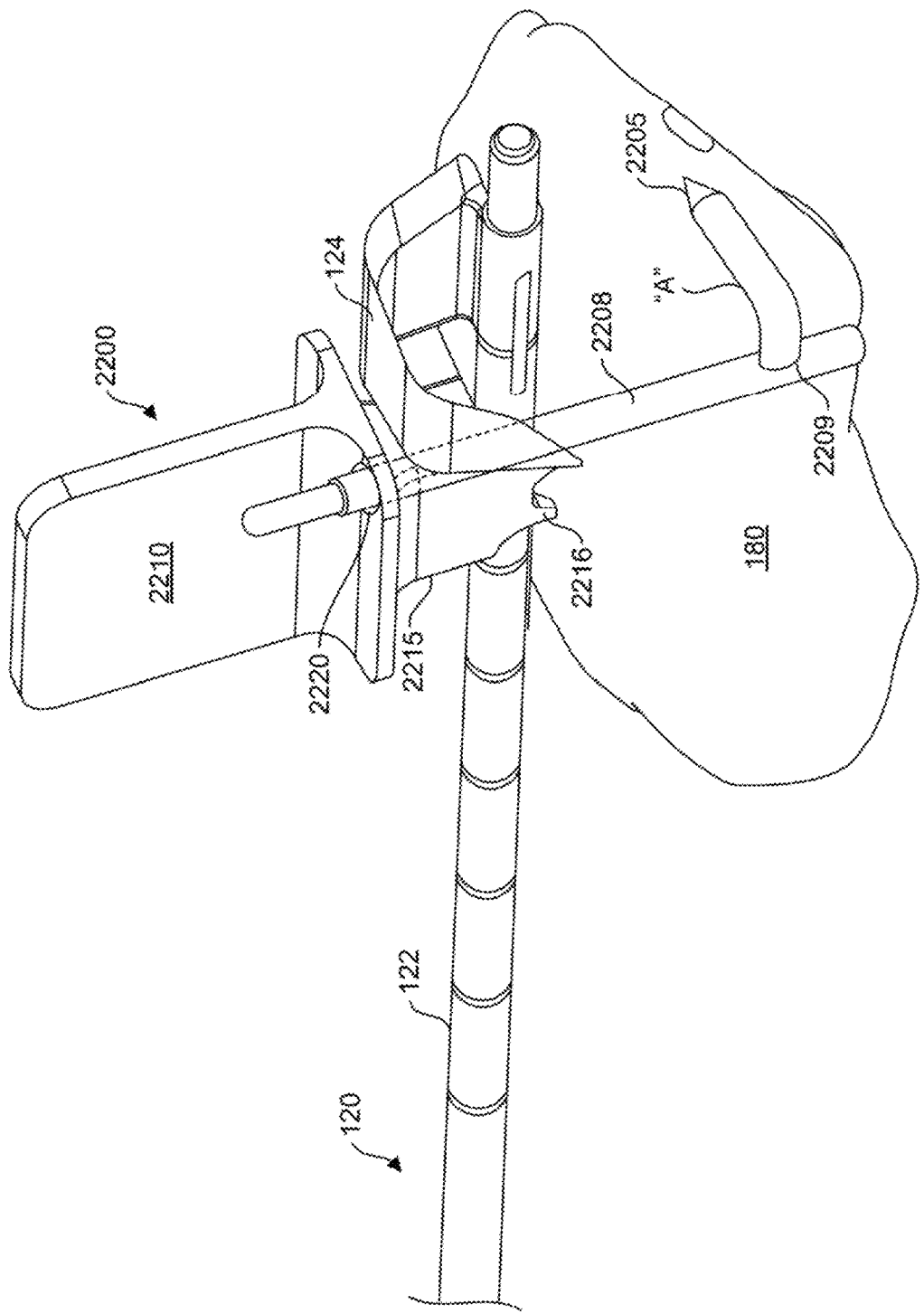

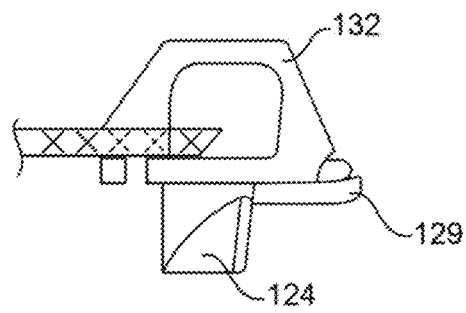 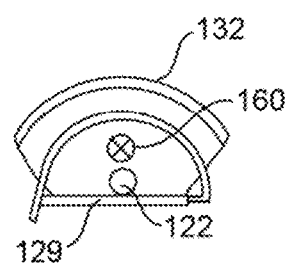 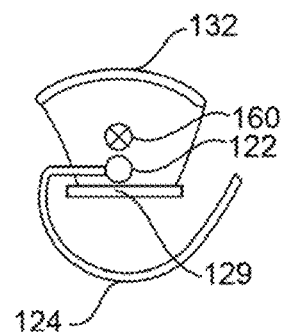
FIG. 10A    FIG. 10B    FIG. 10C
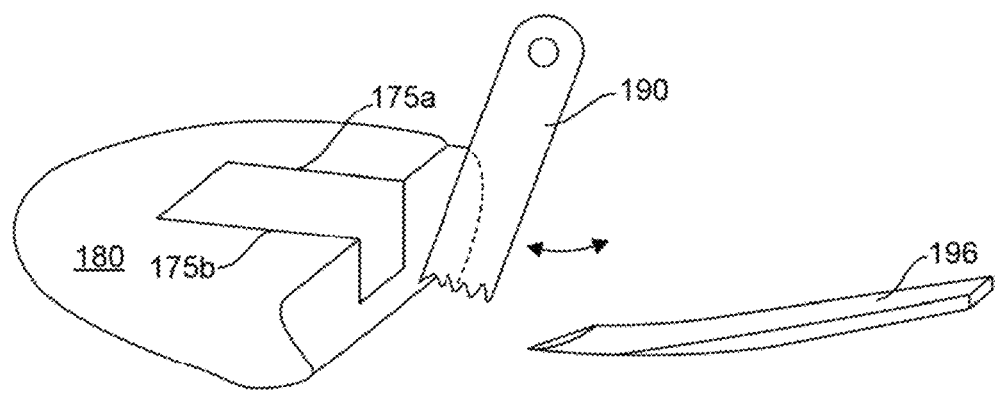
PRIOR ART
FIG. 11A

TENDON HARVESTING SYSTEM

CROSS REFERENCE TO RELATED APPLICATIONS

This application is a U.S. National Phase Entry of PCT Application Serial No. PCT/US19/054486 filed Oct. 3, 2019 and titled "TENDON HARVESTING SYSTEM", which claims the benefit of U.S. Provisional Application No. 62/741,964, filed Oct. 5, 2018, entitled "TENDON HARVESTING SYSTEM", the entirety of which is incorporated herein by reference in its entirety.

FIELD OF THE INVENTION

The present invention relates to the field of surgery and, more particularly, to instruments and methods of harvesting quadriceps tendons.

BACKGROUND

The quadriceps tendon (QT or Quad Tendon) is oftentimes harvested as a graft for ligament surgery such as anterior cruciate ligament (ACL) revisions/reconstructions. This tendon is located on the superior aspects of the patella on the anterior aspect of the thigh. Currently graft harvesting from the QT may require large incisions up the longitudinal axis of the femur to cut down to the level of the tendon, resulting in large postoperative scars. Alternatively harvesters are available, offering smaller incisions that advance blindly in a proximal direction from the knee towards the quadriceps muscle. Care must be taken while harvesting to avoid penetration of the water-tight capsule surrounding the knee joint as this would allow saline to extravasate up into the extracapsular region and potentially up in the groin area. Joint pressure may also be lost, and therefore distention and visualization of the knee joint during ACL reconstruction. Since the preferred portion of the QT for harvesting is attached to the capsule with no natural separation plane, there is a need for a system and techniques for harvesting a graft safely, while protecting the capsule, providing a consistently good-quality graft with high cosmetic results that is simple and easily reproducible. In addition, since tendon harvesters typically advance blindly in a proximal direction there is a need for simply and reliably terminating the graft at the proximal end.

In addition, when tendons are harvested with a bone block attached, a bone block is typically cut using straight cuts, leaving sharp angles in the patella that may fracture. Therefore there is a need for a system to remove at least one bone block, and up to two that has a rounded cross-section, to reduce complications associated with stress fractures.

BRIEF DESCRIPTION OF THE DRAWINGS

For a detailed description of example embodiments, reference will now be made to the accompanying drawings in which:

FIG. 1G schematically shows an isometric view of an alternative embodiment of a harvesting tool guide in accordance with at least some embodiments;

FIGS. 10A, 10B and 10C show a side view, a cross-section view of a cutting portion of a harvesting tool in a first position and a cross-section view of a cutting portion of a harvesting tool in a second position respectively with a scope, in accordance with at least some embodiments;

FIG. 11A shows a known method of creating a bone block, according to existing prior art;

SUMMARY

Figure 1A:
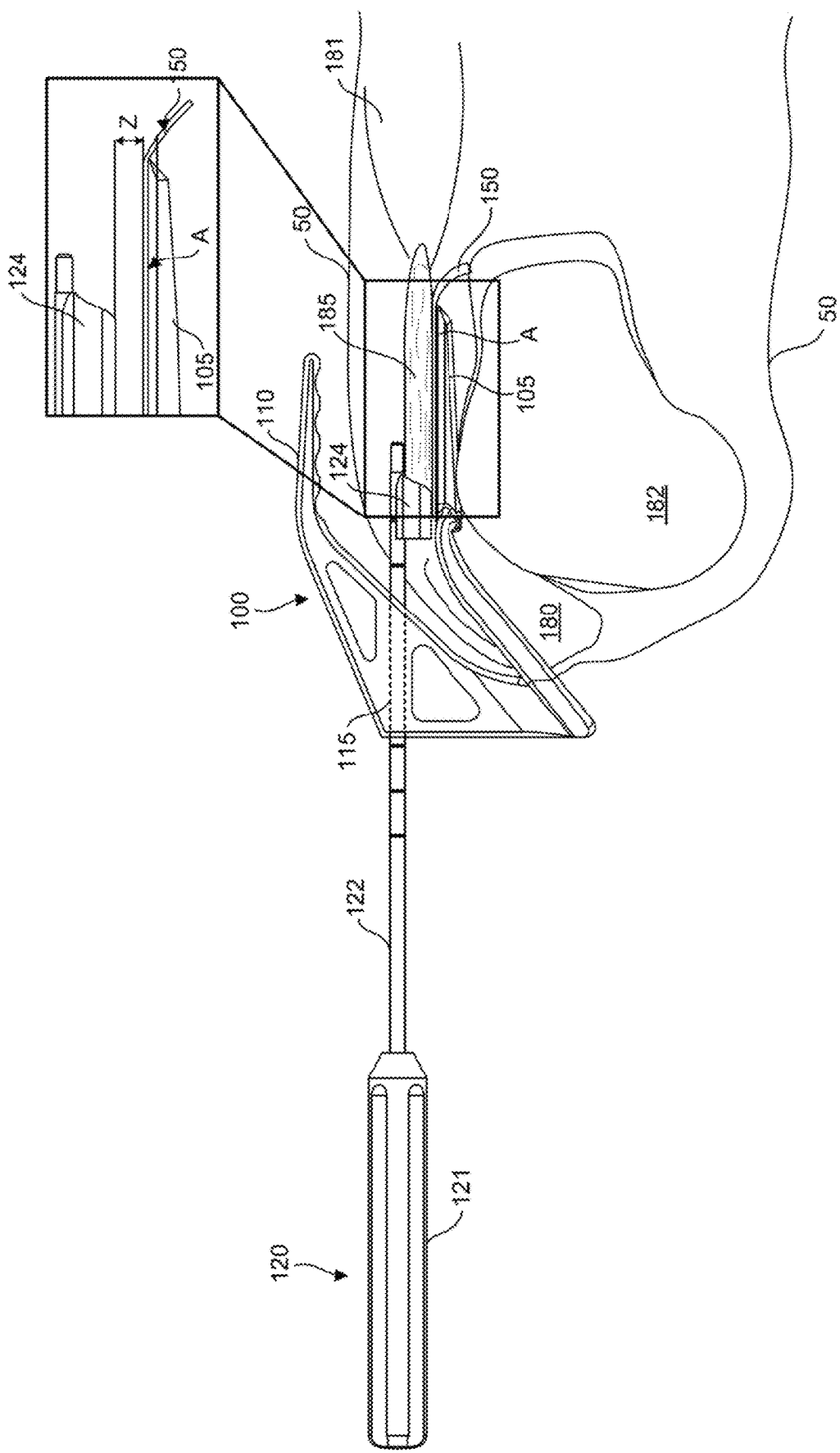
FIGS. 1A and 1B schematically show a side view and end view respectively of a harvesting system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to a Quadriceps Tendon Harvesting System for use in procedures, such as arthroscopic procedures. More particularly, example embodiments are directed to a surgical instrument for producing or harvesting a graft from a tendon, the instrument having a handle, a shaft and a blade portion operatively coupled to the shaft. The blade portion includes a leading cutting edge that has a length and extends around the blade portion, the cutting edge at least partially defining a resulting cross section of the graft. The blade portion is configured to be initially rotatingly inserted into the tendon. Rotating the shaft around the longitudinal axis of the shaft rotates the blade portion to insert it into the tissue. Once inserted, the cutting edge portion may now be disposed within the tendon defining both the thickness and width of the resulting graft.

In some embodiments, the blade portion may have a first end coupled to the shaft and a second end that is free, the cutting edge extending therebetween. The second end may be tapered or shaped to ease initial insertion of the blade portion into the tendon while rotating. Stated otherwise the second end may be configured to initially pierce the tendon as the blade portion is axially rotated to be inserted into the tendon. In some more specific embodiments the cutting edge may be shaped to form a posterior surface and at least two lateral surfaces of the graft simultaneously as the cutting edge translates along the tendon. In other more specific embodiments the instrument may include a surfing element directly coupled to the blade portion first end to the shaft. The surfing element may surf along the external surface of the tendon and control a pathway of the cutting edge as the cutting edge cuts along the tendon. In some of the embodiments the surfing element may extend between the shaft and the blade portion first end unilaterally, leaving an opening on the opposing side of the shaft between the blade portion free end and the shaft. In some of the embodiments the cutting edge may define shape that produces a graft cross section that is a rectangle. In some embodiments the cutting edge may define a shape configured to product a graft cross section that is a partial circle, and may be a semi-circle. In some of the embodiments the surgical instrument may further comprise amputating means for selectively terminating the graft, the shaft having a longitudinal axis and wherein the amputating means comprises a means of changing an orientation of an end portion of the cutting edge to a non-zero angle relative to the longitudinal axis. In some embodiments these means of changing an orientation of an end portion of the cutting edge comprises an outer straight tube and an inner shaft coaxially disposed and axially slideable relative to the outer shaft. The inner shaft may be formed of a flexible material that is pre-formed so as to curve away from the shaft longitudinal axis as it axially slides and releases from the outer tube, and wherein the inner shaft is operatively coupled to the blade portion such that axially sliding the inner shaft moves the cutting edge along a trajectory at non-zero angle to the shaft longitudinal axis.

Another example surgical instrument embodiment is disclosed, for producing a graft from a tendon including a handle, a shaft and a blade portion. The blade portion is operatively coupled to the shaft and includes a cutting edge. The blade portion may be shaped to form an aperture for receiving graft tissue therethrough, The blade portion may be moveable between a first orientation configured to produce a graft having a length parallel to a shaft longitudinal axis and a second angled orientation configured to amputate the graft. In some of the embodiments the blade portion has a tapered free end to pierce the tendon while axially rotatingly inserting the blade portion, about the shaft longitudinal axis, into the tendon and place the tendon within the aperture. In some of the embodiments the cutting edge may shaped to form a posterior surface and two lateral surfaces of the graft simultaneously as the cutting edge translates along the tendon. In some of the embodiments, the shaft may include an outer straight tube and an inner shaft, coaxially disposed and axially slideable relative to the outer shaft, the inner shaft formed of a flexible material that is pre-formed so as to curve away from the shaft longitudinal axis as it axially slides to move the blade portion into the second angled orientation. In some of the embodiments the shaft may alternatively have a hinge adjacent the blade portion configured to selectively hinge and move the blade portion away from the shaft longitudinal axis and to the second angled orientation.

An example method of forming a strip of tendon graft is also disclosed including the steps of: placing a blade portion of a harvesting device external to and directly adjacent an external surface of the tendon and axially rotating the blade portion so as to pierce the external surface of the tendon with a blade portion free end at a first location. The blade portion is further rotated until the free end is disposed adjacent the external surface at a second location, and may exit the tendon tissue. The second location may be laterally spaced relative to the first location, placing the blade portion in a first inserted orientation. The blade portion may then be axially translated along the tendon to form the strip of tendon graft while the blade portion is in this first inserted orientation. In the example method axially rotating the blade portion may moves a surfing element of the harvesting device towards the first location and away from the second location. While axially translating the blade portion, the surfing element may engage with the tendon external surface. The example method may also include sliding the graft strip through an aperture of the blade portion while axially translating the blade portion. The example method may also include changing the blade portion orientation so as to be angularly oriented or angularly elevated relative to the inserted configuration and directed toward the tendon external surface and amputating an end of the graft strip. The example method may also include changing the blade portion orientation by axially extending a shaft having a preformed curve, the shaft operatively coupled to the blade portion.

In other example embodiments, a guide is disclosed for maintaining an offset while stripping a tendon that may have an elongate leg that slides under and along a length of a knee capsule, a handle for applying tension to the elongate leg and thereby the knee capsule, and an opening disposed through a portion of the guide. The opening may receive a shaft of a device for stripping the tendon, the opening sized and shaped so as to maintain an offset between the knee capsule and device as the device extends through said opening. The opening may define an elongate axis that is generally parallel to an elongate axis of the elongate leg. The guide may be generally a U, L, or C shape, with two sides or two legs, and wherein the handle defines one leg and the elongate leg the other leg. The opening may have a lateral opening for receiving the device from a lateral side of the guide. The guide may have a jogged or lateral offset portion extending between the opening and elongate leg, so as to route the guide around a patella and yet keep the elongate leg and opening medially disposed in order to enter the capsule via standard portals. The guide may define a medial plane that the handle, elongate leg and opening all lie on.

Other example embodiments are directed to a tendon cutter for removing a portion of a tendon, having a handle at a first end, a cutting portion and a top surface element at the other end and a shaft therebetween. The cutting portion may define a rounded cross-section, that may be semicircular or U shaped cross section and the top surface element acts like a surfboard so as to lie on and slide along a surface of the tendon. This top surface element may control movement of the cutting portion into the tendon, preventing the cutting portion from moving too far into the QT, minimizing variation in the resulting graft thickness. The cutting portion may rotate from a first position wherein the cutting portion is disposed external to the tendon to a second position wherein the cutting portion is disposed within the tendon. The cutting portion may have two cutting edge portions at an angle to each other, including a first cutting edge orthogonal to the shaft longitudinal axis and a second cutting edge extending from the first cutting edge and oriented at an acute angle from the first cutting edge; the second cutting edge aiding insertion or cutting into the tendon. The tendon cutter may also include a shroud that at least partially shields the cutting portion from adjacent tissue when in the first position. The tendon cutter may also have a scope selectively coupled to the shaft and terminating adjacent the cutting portion, to aid in real time location of the cutter.

Other example embodiments are directed to a bone plug harvesting system for harvesting a rounded cross-section bone block, including a trephine and an aligner and may also include a spherical bone drill. The aligner may include a leg that abuts with an anterior surface of the patella top surface, to use as a point of reference. The leg also lies along the anterior surface of the QT and when a trephine is inserted over the leg, the trephine inner lumen and leg cooperate to align the trephine with the patella. The trephine may also have an elongate angular gap, so as to slide over a tendon strip that is continuous and still gain access to the patella. The trephine may include a driving series of gears that includes two gears with at least a first angular gap therebetween, the first angular gap a function of the elongate angular gap of the trephine, so as to drive the trephine from a perpendicular angle and accommodate the angular gap.

DETAILED DESCRIPTION

Various embodiments are directed to a QT Harvesting System and a methods of use. In some embodiments, the harvesting tool system includes a means of forming lateral and posterior surfaces a graft in a single motion while limiting a trajectory of a tendon harvester as the tendon harvester extends along the QT. Limiting any posterior and sometimes also anterior migration may control to a more uniform graft thickness. In addition limiting posterior migration may limit injury to the knee capsule. The means may include a harvesting tool guide with a reference surface that may engage a portion of the knee anatomy such as the patella or knee capsule. The tendon harvester may operatively couple to the guide so as to offset the tendon harvester and direct the pathway of the tendon harvester while cutting, based on this reference surface. Alternative or supplemental means of limiting the trajectory may include a surfing surface on the tendon harvester that maintains a portion of the tendon cutter on an anterior surface of the QT.

In some embodiments the tendon cutter may include means of selectively terminating an end of the strip removed from the QT. The specification now turns to an example system.

Harvesting Tool Guide

A first example system may include a guide, which generally includes a reference surface such as a bar or leg configured to be placed underneath the knee capsule and an opening for guiding a harvesting tool therethrough. The opening may be configured to control the path of the harvesting tool and maintain an offset between the harvesting tool cutting path and the reference surface that is engaged with the knee capsule. The guide may include a handle that may not only aid in placing the guide in the targeted location but also apply a tension to more positively engage the knee capsule. This may provide a more reliable and consistent spacing between the cutting portion pathway of the harvesting tool and the knee capsule. The harvesting tool may be configured to cut while moving away from or towards the knee. Turning to the embodiment schematically shown in FIGS. 1A and 1B, the present invention includes a Quadriceps Tendon (QT) harvesting system that includes a guide 100 and harvester 120. The guide 100 is generally configured to limit the motion of a tendon harvester 120 relative to a knee capsule 150, so as to maintain a pre-set minimum offset between the tendon harvester 120 and knee capsule 150, reducing the likelihood of the tendon harvester 120 puncturing the knee capsule 150. The knee capsule 150 is a water-tight capsule or cavity surrounding the knee joint, advantageous for arthroscopic operations. For example control of the fluid environment within this cavity allows the working area around the ACL to be distended, increasing working space. Flushing of the cavity also improves visualization. Puncturing of this water-tight cavity may cause complications associated with a lack of control of this fluid environment. It may also permit extravasation, potentially up to the groin area.

As shown the knee capsule 150 is attached to a portion of the QT 185 and can therefore potentially be cut while stripping the QT 185, the stripping preparing a portion of the QT 185 to be transferred as a graft for a ligament reconstruction. The guide 100 therefore provides a means of maintaining an offset between a tendon cutting portion of a tendon harvester 120 and the capsule 150 and comprises an elongate bar 105 that is configured to be inserted through the skin at a location near the patella 180, and then extend along a substantial portion of the QT length towards the quadriceps muscle 181, between the capsule and femur 182. Elongate bar 105 therefore provides a reference surface, as described earlier. Elongate bar 105 may have a tapered end to ease insertion through skin 50 and between the tissues, but sufficiently rounded so as to not puncture or damage the capsule 150 or cartilage. Bar 105 may also have a smooth surface to ease insertion and a sleeve/cannula to protect cartilage. The guide 100 may also include an opening 115 for receiving a tendon harvester 120, the opening 115 configured to maintain the harvester 120 along a path that is offset a predetermined minimum distance "Z" from the reference surface of bar 105 and thereby offset from the capsule 150. "Z" is defined as a distance between anterior surface "A" of bar 105 to a posterior surface of cutting portion 124. More specifically the opening 115 is offset from an inner elongate surface A of the bar 105 and opening 115 may be parallel to surface A. In other embodiments, opening 115 may be angled relative to surface A, configured so as to aim the harvester 120 at an angle, away from reference surface A, such that distance "Z" increases as the harvester 120 extends proximally along the QT. This embodiment may help if the QT grows overly thick towards its proximal end. The portion of the guide including the opening 115 is configured to remain external to the patient with the bar 105 inserted. Opening 115 may be sized so as to allow sliding of a harvester shaft 122 therethrough, and also rotation of the harvester shaft 122 (and thereby cutting portion 124) but also sized to maintain the offset pathway, or a minimal offset from surface A. Stated otherwise, the opening 115 should not allow significant play between the harvester 120 and guide 100 such that the offset "Z" has sufficient movement so as to potentially puncture capsule 150. The inventor also envisions alternate coupling and controlling means for maintaining the minimum offset "Z", including sliding coupling means such as a rail system that slidingly connects to harvester shaft 122; or alternatively the guide may include a shaft that slides within a portion of the harvester shaft 122. In further alternative embodiments the harvester shaft 122 could fixedly couple in translation (not in rotation) to the guide 100 and move with the elongate leg 105, as the leg 105 slides under the knee capsule.

In some embodiments opening 115 may be a "c" shaped opening, and therefore not a completely enclosed opening so that a shaft 122 of harvester 120 can slide in from the side.

Guide 100 may also include a handle 110, configured to remain external to the patient, and pulling on the handle 110 aids in maintaining the offset. Handle 110 may be flexible so as to limit the tension applied to the bar 105. Generally the guide 100 is a "U" shaped construct, that may be constructed as a single element, with the bar 105 defining a first leg of the "U" and the handle 110 defining the second leg of the "U", with the opening 115 disposed therebetween, through a portion bridging the two legs.

During use, guide 100 may first be placed under the knee capsule 150 to a proximal end of the QT. Guide 100 may then be controlled to improve engagement between the knee capsule and a reference surface of the guide. Guide handle 110 may be lifted in an anterior direction for example. Harvesting tool 120 may then be coupled to guide 100 with the cutting portion 124 towards a distal end of QT (near the knee). Cutting portion 124 may initially be anteriorly spaced and external to the QT. Shaft 122 may then be axially rotated to insert the cutting portion 124 into or posterior to the QT. Cutting portion 124 may then be advanced proximally to form a QT graft, the cutting portion pathway at least partially defined and limited by the guide 100. In some embodiments the harvesting tool 120 may be coupled to guide 100 with the cutting portion 124 towards a proximal end of QT. Cutting portion 124 may be anteriorly spaced from QT and then rotated to insert the cutting portion 124 into or posterior to the QT. Cutting portion 124 may then be advanced distally, towards the knee to form a QT graft, the cutting portion pathway at least partially defined and limited by the guide 100.

Figure 1B:
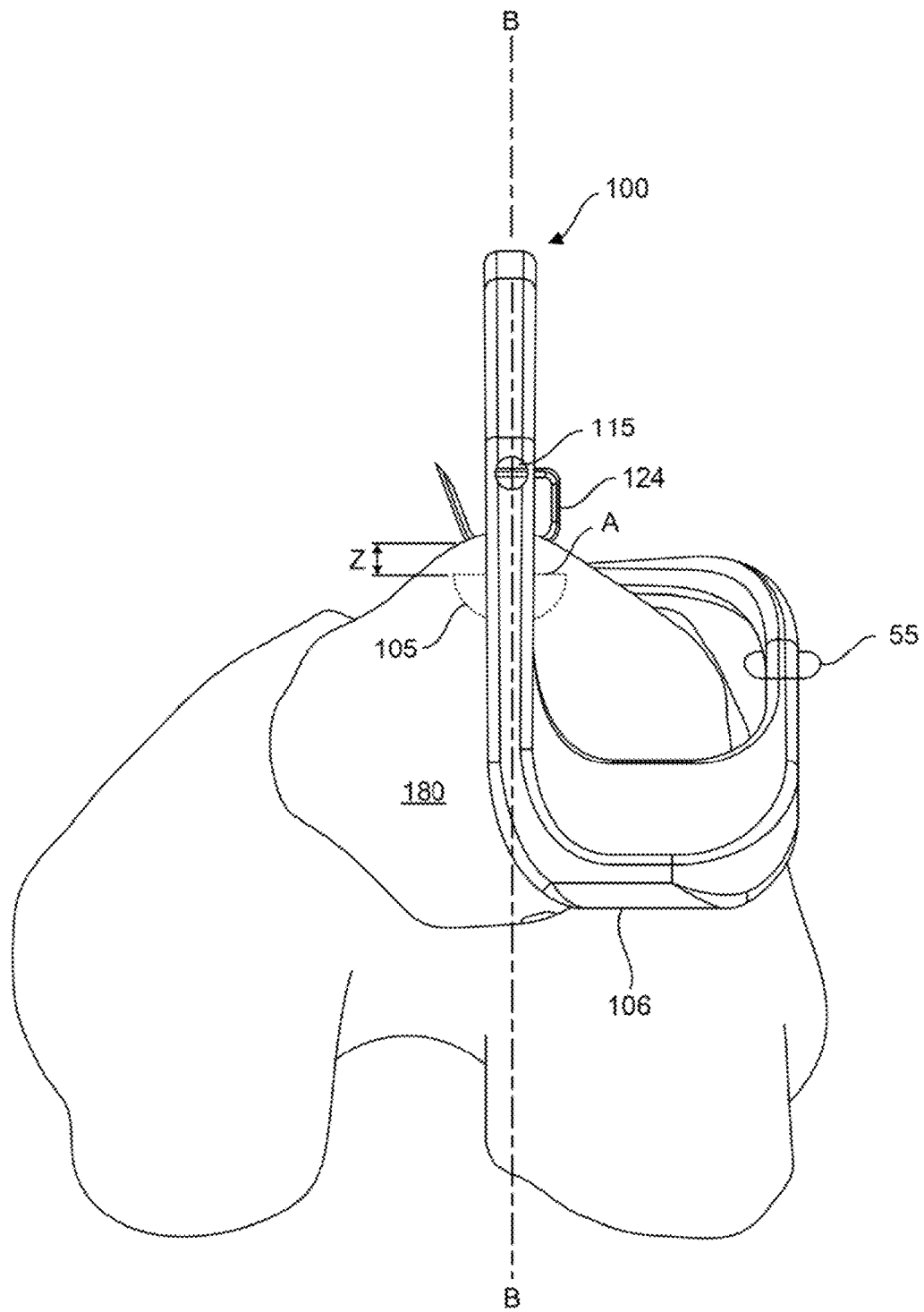

Best seen in FIG. 1B the guide 100 comprises a lateral offset portion 106, operable to route the guide 100 around the patella 180 from a standard portal, then centrally place the bar 105 underneath the capsule 150. Portals through the skin during surgery are typically disposed both sides, either side of the patella 180, and therefore offset from the more centrally disposed QT 185. The lateral offset portion 106 is offset so as to position the bar 105 centrally and under the QT 185 and capsule 150 while the lateral offset portion 106 of the guide 100 is disposed in the offset standard portal 55, representatively shown in FIG. 1B. The lateral offset portion 106 begins and ends on the same vertical plane that extends through axis B-B such that the opening 115 and a bar 105 and handle 110 are on the same plane and centrally disposed under the QT. Stated otherwise bar 105 and opening 115 may be in line with each other.

Figure 1C:
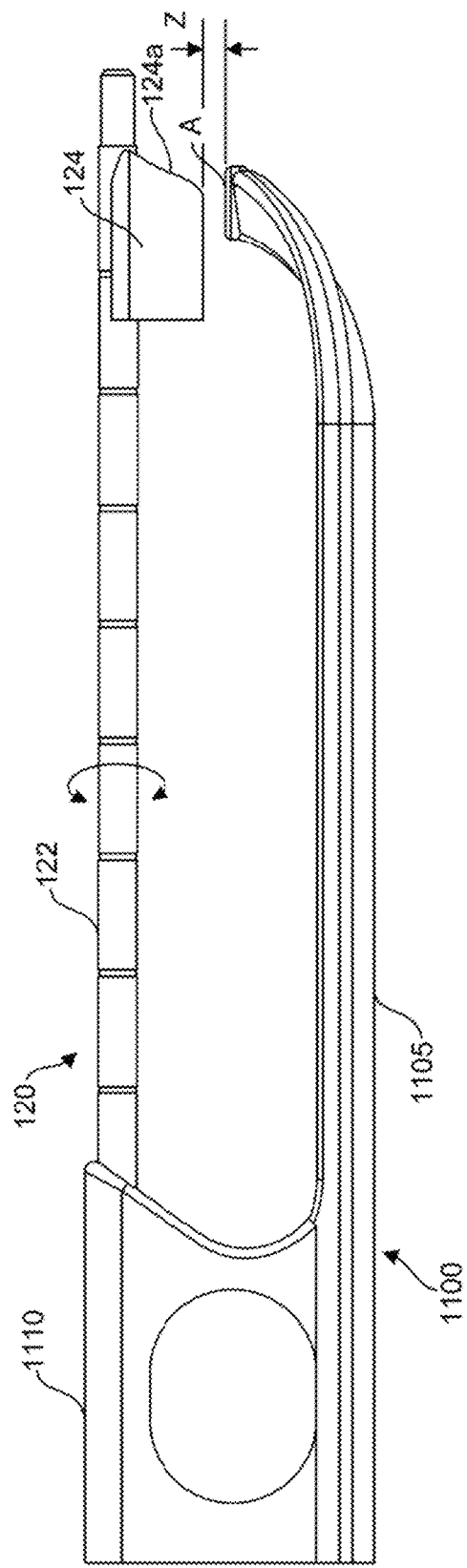
FIGS. 1C and 1D schematically show a side view and end view respectively of an alternative embodiment of a harvesting system in accordance with at least some embodiments.
Figure 1D:
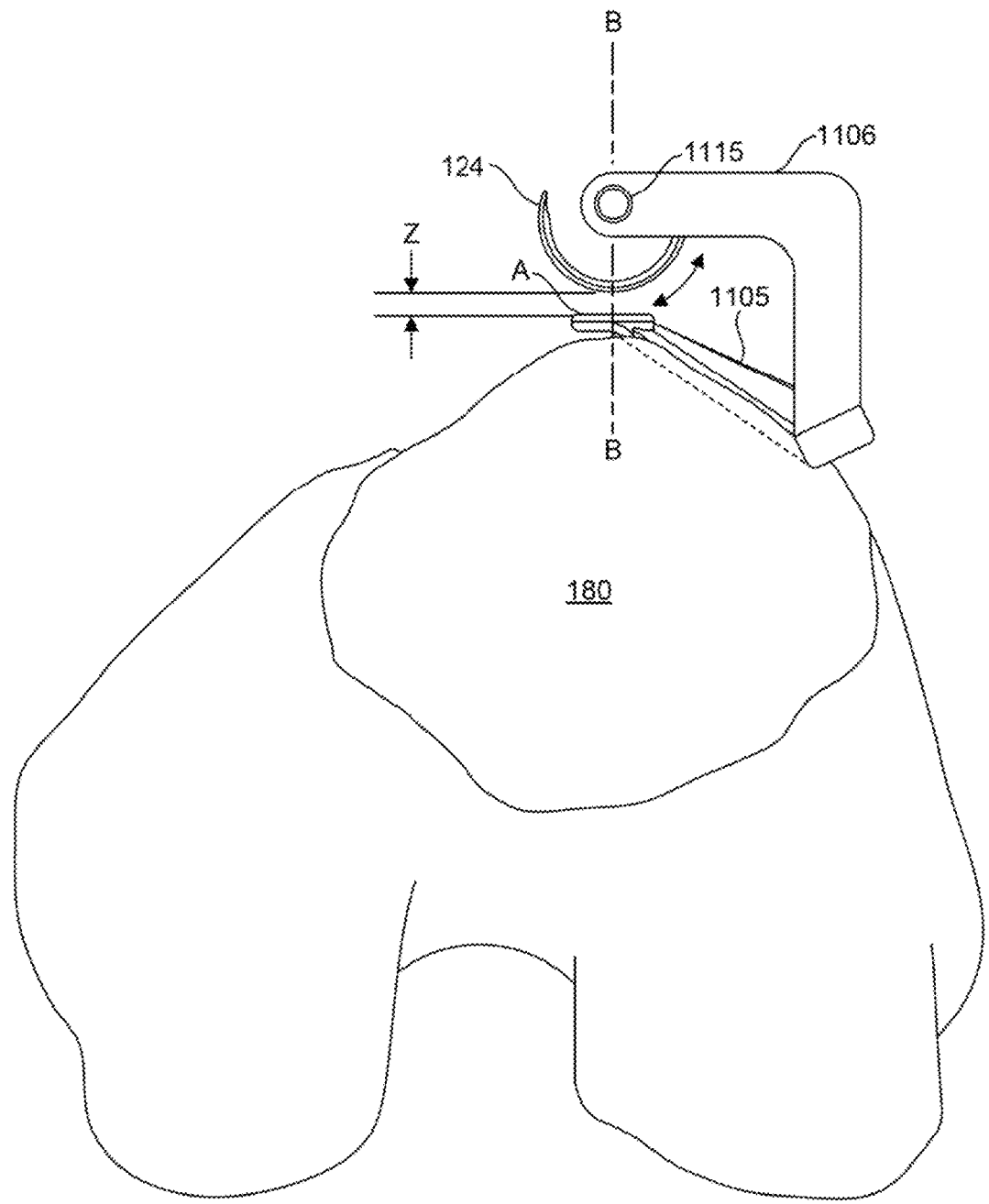

Shown in FIG. 1C, is an alternative embodiment of a Quadriceps Tendon (QT) harvesting system that includes guide 1100. Similar to the previously described guide, guide 1100 provides a means of maintaining an offset between a tendon cutting portion 124 of a tendon harvester 120 and the capsule 150 (not shown in this FIG. 1C) and comprises an elongate bar 1105 that is configured to be inserted through the skin at a location near the patella 180 (not shown), and then extend along a substantial portion of the QT length towards the quadriceps muscle 181, between the capsule and femur 182, similar to bar 105 in a previous embodiment. Bar 1105 may therefore have a tapered end to ease insertion through skin and between the tissues, but sufficiently rounded so as to not puncture or damage the capsule 150 or cartilage. Bar 1105 may also have a smooth surface to ease insertion and a sleeve/cannula to protect cartilage. Bar 1105 may include a reference surface "A" that may slide underneath knee capsule 150. Reference surface may be shorter in this embodiment as the reference surface "A" and cutting portion 124 translate simultaneously. Surface "A" in this embodiment may extend directly underneath (posterior) the leading edge (124a) of cutting portion. Stated otherwise the reference surface "A" and cutting portion leading edge 124a are maintained so be axially coincident or axially overlap each other. Guide 1100 may also include an opening 1115 for receiving a portion of the tendon harvester 120, the opening 1115 configured to maintain the harvester 120 along a path that is offset a predetermined distance "Z" from the bar 1105 and thereby offset from the capsule 150. "Z" is defined as a distance between anterior surface "A" of bar 1105 to a posterior surface of cutting portion 124. More specifically the opening 1115 is offset from surface "A" of the bar 1105 and opening 1115 may be parallel to surface "A". In other embodiments, opening 1115 may be angled relative to surface A, configured so as to aim the harvester 120 at an angle, away from surface A, such that distance "Z" increases as the harvester 120 extends along the QT. This embodiment may help if the QT gets overly thick towards its proximal end. The portion of the guide including the opening 1115 is configured to remain external to the patient with the bar 1105 and cutting portion 124 inserted. Opening 1115 may be sized so as to allow sliding of a harvester 120 therethrough, or may in alternative embodiments be fixed relative to the harvester 120 and only allow rotation. Opening 1115 may be sized to receive a shaft of the harvester 120 or a handle 121 of the harvester. Similar to previous guides described, guide 1110 comprises a lateral offset portion 1106, operable to route the guide 1100 around the patella 180 from a standard portal. Bar 1105 may then be angled or have a jog to centrally place the bar 1105 and more specifically surface "A" more medially and underneath the capsule 150 (not shown). The lateral offset portion 1106 is configured so as to position the bar 1105 centrally and under the QT 185 and capsule 150 while the lateral offset portion 1106 of the guide 1100 is disposed in the offset standard portal. The lateral offset portion 1106 may begin and end on the same vertical plane that extends through axis B-B such that the opening 1115 and bar 1105 are on the same plane and centrally disposed under the QT. Stated otherwise bar 1105 and opening 1115 may be in line with each other. Guide 1110 may have a handle.

Harvester 120 is operatively coupled to guide 1100 so as to slide simultaneously with surface "A" and may therefore be axially fixed relative to handle portion 1110. Harvester 120 may be operatively coupled to guide 100 so as to allow the harvest shaft 122 to rotate about a shaft axis, and move cutting 124 from an anterior side of the QT posteriorly into the QT, as will be explained later. FIG. 1C shows the cutting portion 124 in a posterior cutting position wherein the leading edge 124a is disposed a distance "Z" configuration from reference surface "A". Rotation of the shaft 122 is configured to remove cutting portion 124 from QT and increase distance "Z".

An example method of use may therefore include, placing an end of a guide 1100 under the knee capsule 150 towards a distal end of the QT. Harvesting tool 120 may then be coupled to guide 1100 with the cutting portion 124 axially coincident with reference surface of guide 1100. Cutting portion 124 may be anteriorly spaced from QT. Shaft 122 may then be rotated to insert the cutting portion 124 posteriorly into the QT. Cutting portion 124 and surface "A" may then be advanced proximally to form a QT graft, the cutting portion pathway at least partially defined and limited by the guide 1100. More specifically the cutting portion pathway at least partially defined and limited by the reference surface "A" of guide 1100 and knee capsule 150. In some embodiments the harvesting tool 120 may be coupled to guide 100 with the cutting portion 124 and reference surface "A" towards a proximal end of QT. Cutting portion 124 may be anteriorly spaced from QT and then rotated to insert the cutting portion 124 posteriorly into the QT. Cutting portion 124 and lateral surface "A" may then be advanced distally, towards the knee to form a QT graft, the cutting portion pathway at least partially defined and limited by the guide 1100.

Figure 1E:
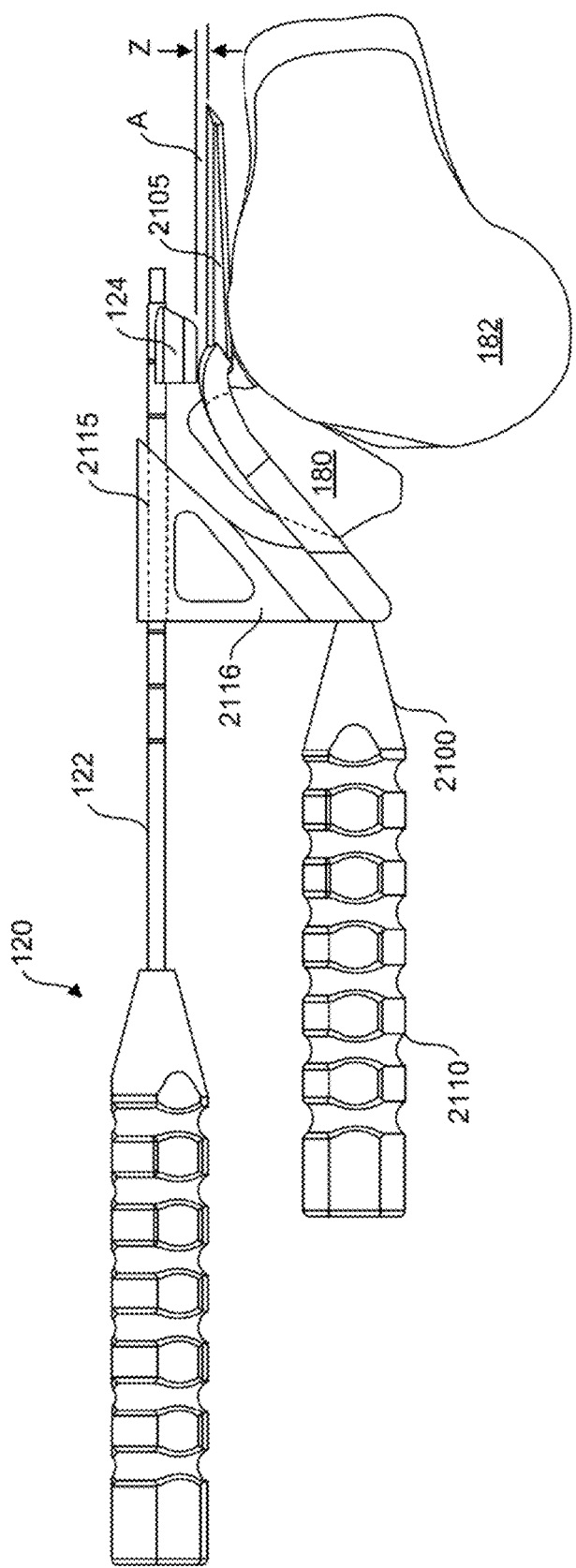
FIGS. 1E and 1F schematically show a side view and end view respectively of an alternative embodiment of a harvesting system in accordance with at least some embodiments.
Figure 1F:
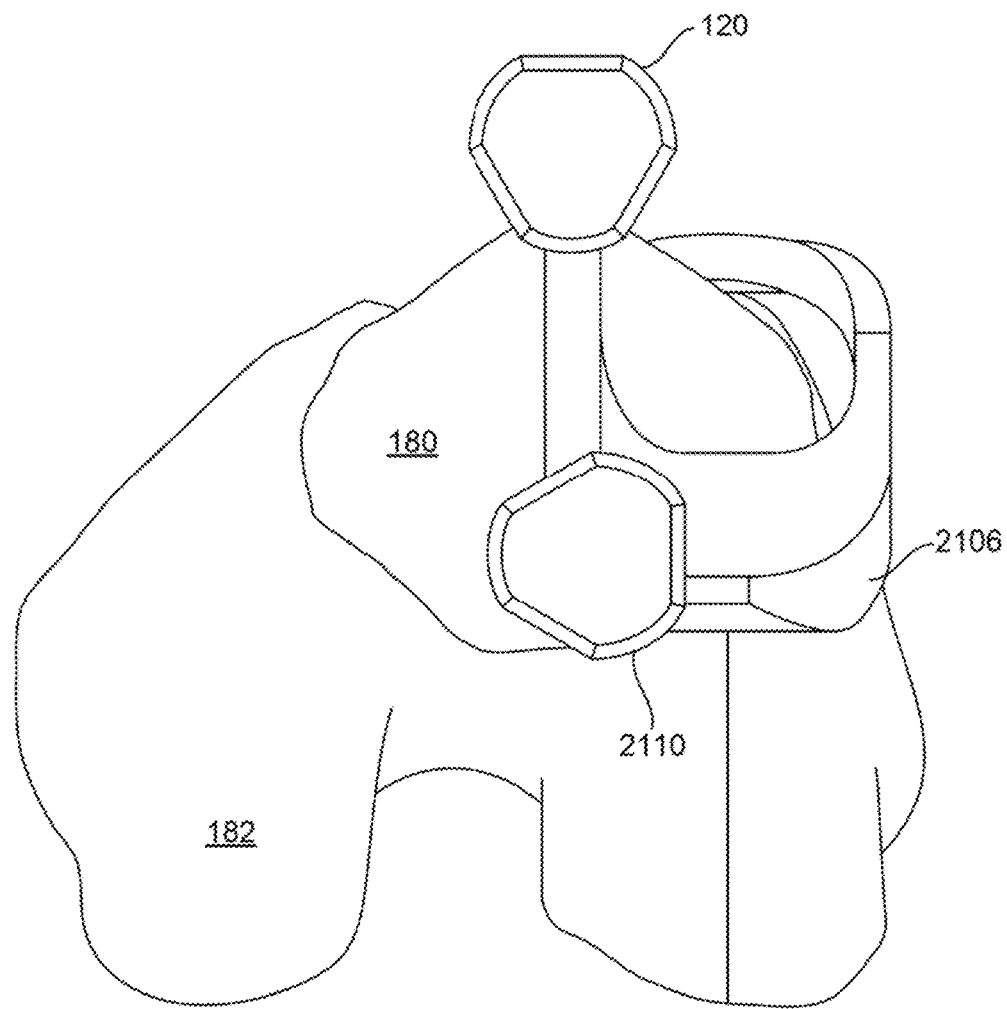

Shown in FIG. 1E, an embodiment of a Quadriceps Tendon (QT) harvesting system may include an alternative guide 2100, configured to limit the motion of a tendon harvester 120 relative to a knee capsule 150. In these figures the knee capsule and QT have been removed for clarity; FIG. 1A shows the removed detail. Similar to the previously described guides, guide 2100 therefore provides a means of maintaining an offset "Z" between a tendon cutting portion 124 of a tendon harvester 120 and the capsule 150 and comprises an elongate bar 2105 that is configured to be inserted through the skin at a location near the patella 180, and then extend along a substantial portion of the QT length towards the quadriceps muscle 181, between the capsule and femur. Bar 2105 provides a reference surface and is similar to bar 105 in FIG. 1A. Guide 2100 may also include handle 2110 for guide manipulation by the user and a housing 2116 attached to the handle 2110; the housing 2116 having an opening 2115 for receiving a portion of the tendon harvester 120, the opening 2115 configured to maintain the harvester 120 along a path that is offset a predetermined distance "Z" from the bar 2105 and thereby offset from the capsule 150. "Z" is defined as a distance between anterior surface "A" of bar 2105 to a posterior surface of cutting portion 124. More specifically the opening 2115 is offset from an inner elongate surface "A" of the bar 2105 and opening 2115 may be parallel to surface "A". In other embodiments, opening 2115 may be angled relative to surface A, configured so as to aim the harvester 120 at an angle, away from surface A, such that distance "Z" increases as the harvester 120 extends along the QT. The handle 2110 including the opening 2115 is configured to remain external to the patient with the bar 2105 inserted. Opening 2115 may be sized so as to allow sliding of a harvester 120 therethrough. Opening 2115 may be sized to receive a shaft of the harvester 120. In this embodiment, similar to the embodiment shown and described in FIGS. 1A and 18 the harvester 120 may slide independently of guide 2100. Similar to previous guides described, guide 2100 comprises a lateral offset portion 2106. In this embodiment, handle 2110 may be disposed axially offset from leg 2105.

Shown in FIG. 1G, the present invention may alternatively include a Quadriceps Tendon (QT) harvesting system that includes a keeper 2200, configured to limit the motion of a tendon harvester 120 relative to a knee capsule 150 (not shown for clarity of figure). In this embodiment keeper 2200 provides a means of maintaining the harvester 120 position relative to the patella 180 and comprises a handle 2210 and an opening 2215 configured to receive a portion of the harvester 120. Opening 2215 may be at least partially defined by the patella 180. In operation opening 2215 is defined at least partially by a plurality of spikes 2216 that may be pushed against a patella 180 to restrict motion of harvester 120, thereby providing one means of limiting motion of harvester 120. Spikes may help engage keeper with patella. In some embodiments a spring loaded construct (not shown) within the keeper 2200 may further aid in pushing harvester 120 against patella 180. Similar to the previously disclosed constructs including elongate bars (105, 1105, 2105), a preformed leg 2205 may be inserted vertically through the keeper 2200, and then extend across a portion of the QT, between the capsule and femur 182. This leg 2205 may be used to set an offset at the beginning of the cutter stroke, and may not necessarily extend along the QT length in a proximal direction. In one embodiment, leg 2205 may be kept in a straightened orientation within a hollow shaft 2208, and shaft 2208 may slide though keeper vertical opening 2220. In alternative embodiments, shaft 2208 may also be curved, and may be introduced through a rotary motion. Vertical shaft 2208 may include a depth stop to limit motion of shaft into the tissue. Once shaft end is in desired location, leg 2205 may be pushed so as to emerge from shaft end 2209 and relax into the unstressed relaxed curved form, so as to position leg 2205 under the knee capsule 150, similar to legs previously described. FIG. 1G therefore includes a guide 2200 with a keeper portion for engaging a patella (or other tissue) surface and thereby defining a first reference surface for controlling the pathway of a cutting portion 124 of harvester 120 relative to the patella. Keeper may include an opening 2215 for receiving a harvester shaft 122, the opening 2215 may be at last partially enclosed by the patella (or other tissue) surface. Guide 2200 may include a vertical shaft that may be selectively deployable to form a reference surface "A" that may be deployed underneath and laterally across a knee capsule (not shown).

A method of use may include placing at least one spike of a keeper on a patella surface so as to at least partially enclose an opening in the keeper and then inserting a shaft along a lateral side of the patella and then deploying a lateral arm, laterally from the shaft and underneath the knee capsule. Lateral arm may be an elastic material, elastically deformed within the shaft while inserting the shaft and released from the shaft while being deployed under the knee capsule. Lateral arm may define a reference surface "A". Harvester may then be inserted into keeper opening with the cutting portion 124 anteriorly spaced from QT. Shaft 122 may then be rotated to insert the cutting portion 124 posteriorly into the QT. Shaft 122 may then be vertically adjusted relative to surface "A" prior to harvesting. Cutting portion 124 may then be advanced proximally to form a QT graft, the cutting portion pathway at least partially defined and limited by the guide 2200. More specifically the cutting portion pathway may be at least partially defined and limited by at least one of the reference surface "A" of guide 2200, knee capsule 150 and keeper spikes 2216 on patella. Cutting portion 124 may be anteriorly spaced from QT and then rotated to insert the cutting portion 124 posteriorly into the QT.

Figure 1H:
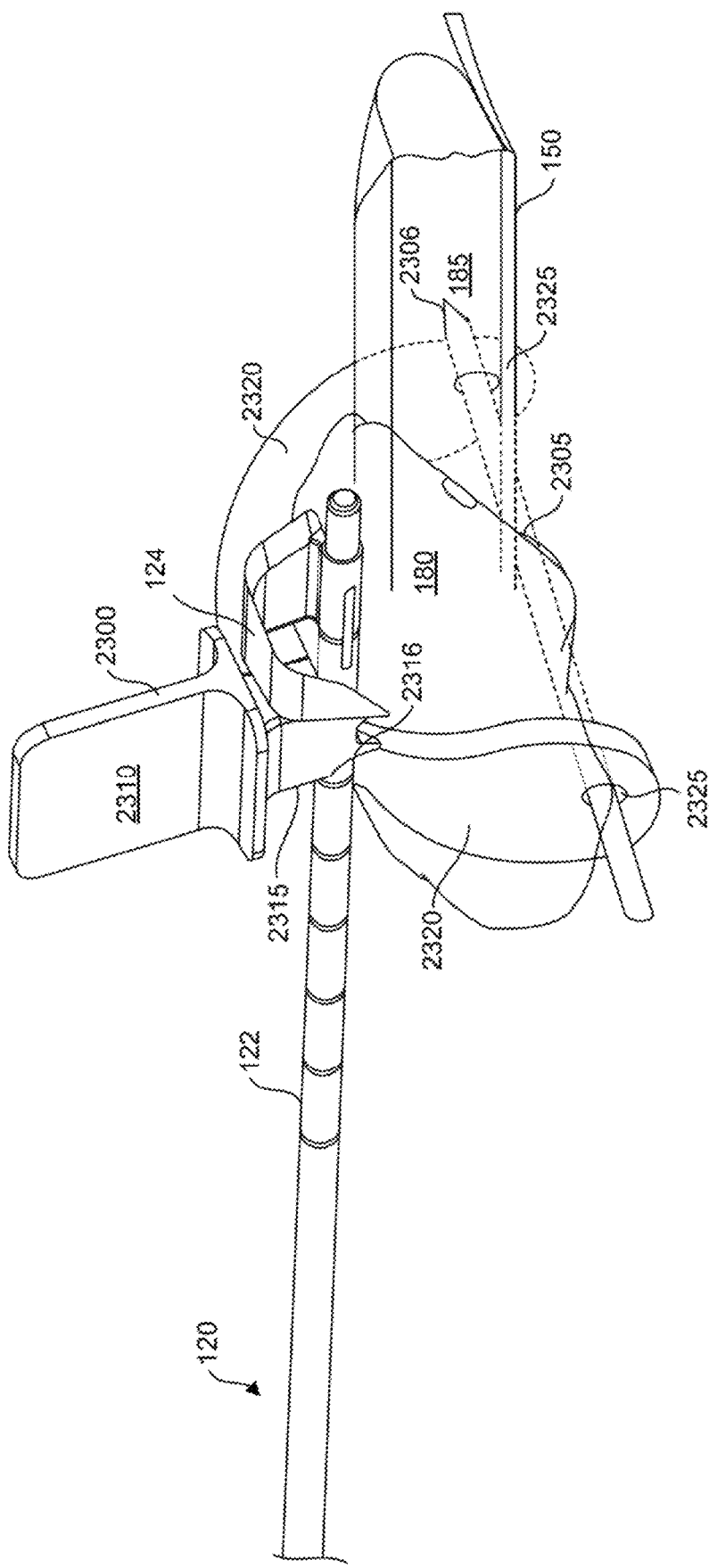
FIG. 1H schematically shows an isometric view of an alternative embodiment of a harvesting tool guide in accordance with at least some embodiments.

Shown in FIG. 1H, is an alternative means of introducing a leg or bar underneath the knee capsule 150, including a keeper 2300 and arm 2320. Keeper comprises a handle 2310 and an opening 2315 configured to receive a portion of the harvester 120. In operation opening 2315 is defined at least partially by spikes 2316 which may be pushed against a patella 180 to restrict motion of harvester 120, similar to the keeper described in FIG. 1G. Seen in FIG. 1H, keeper 2300 may include arm 2320 that extends laterally around the side of patella 180, potentially on both sides, arm 2320 having at least one opening 2325 for receiving and guiding pathway of bar 2305. Bar 2305 may include a pointed end 2306, configured to aid in penetrating through tissues. Bar 2305 is configured to slide underneath knee capsule 150 and operate in a similar manner to bars 105, 2105 etc. Opening(s) 2325 are positioned to as to maintain an offset between an anterior surface of bar 2305 and cutting portion 124, similar to embodiments described before.

Tendon Harvester

Figure 2A:
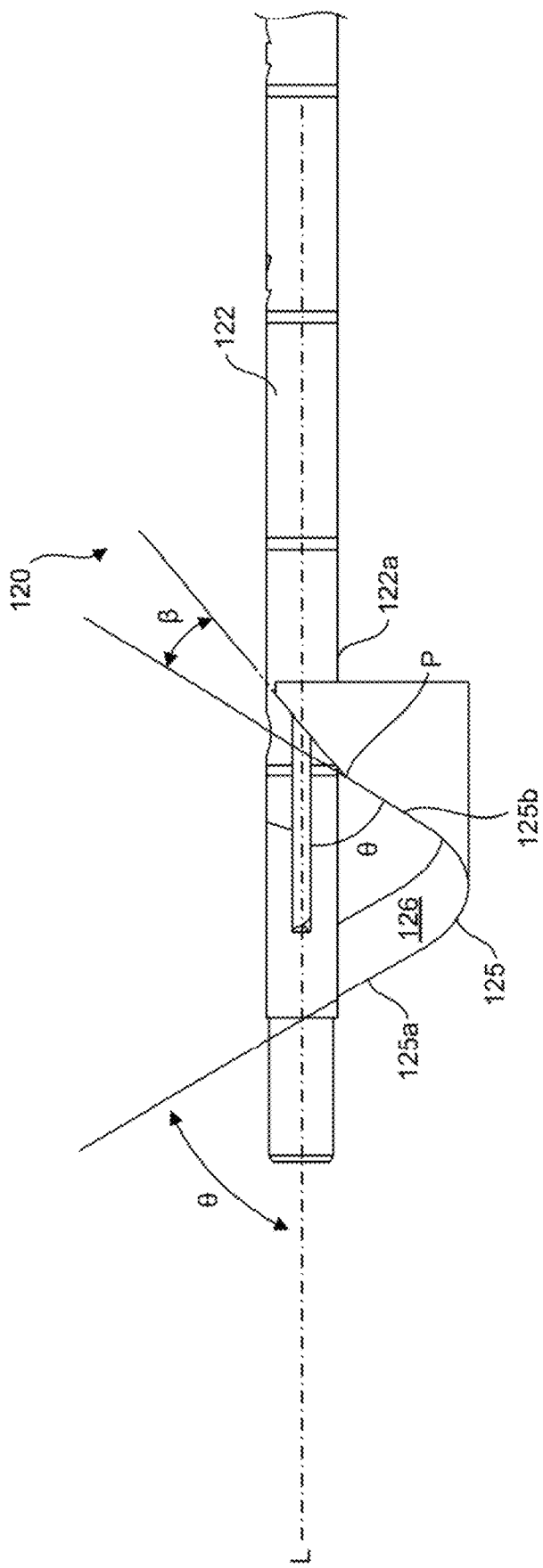
FIGS. 2A, 2B and 2C schematically show a side view, end view and isometric view respectively of a cutting portion of a harvesting tool, in accordance with at least some embodiments.
Figure 2B:
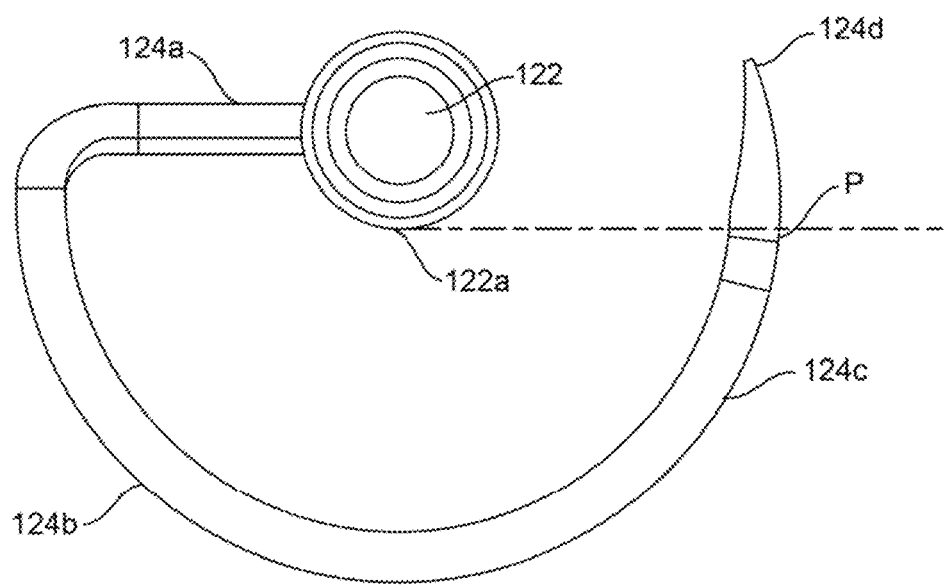
Figure 2C:
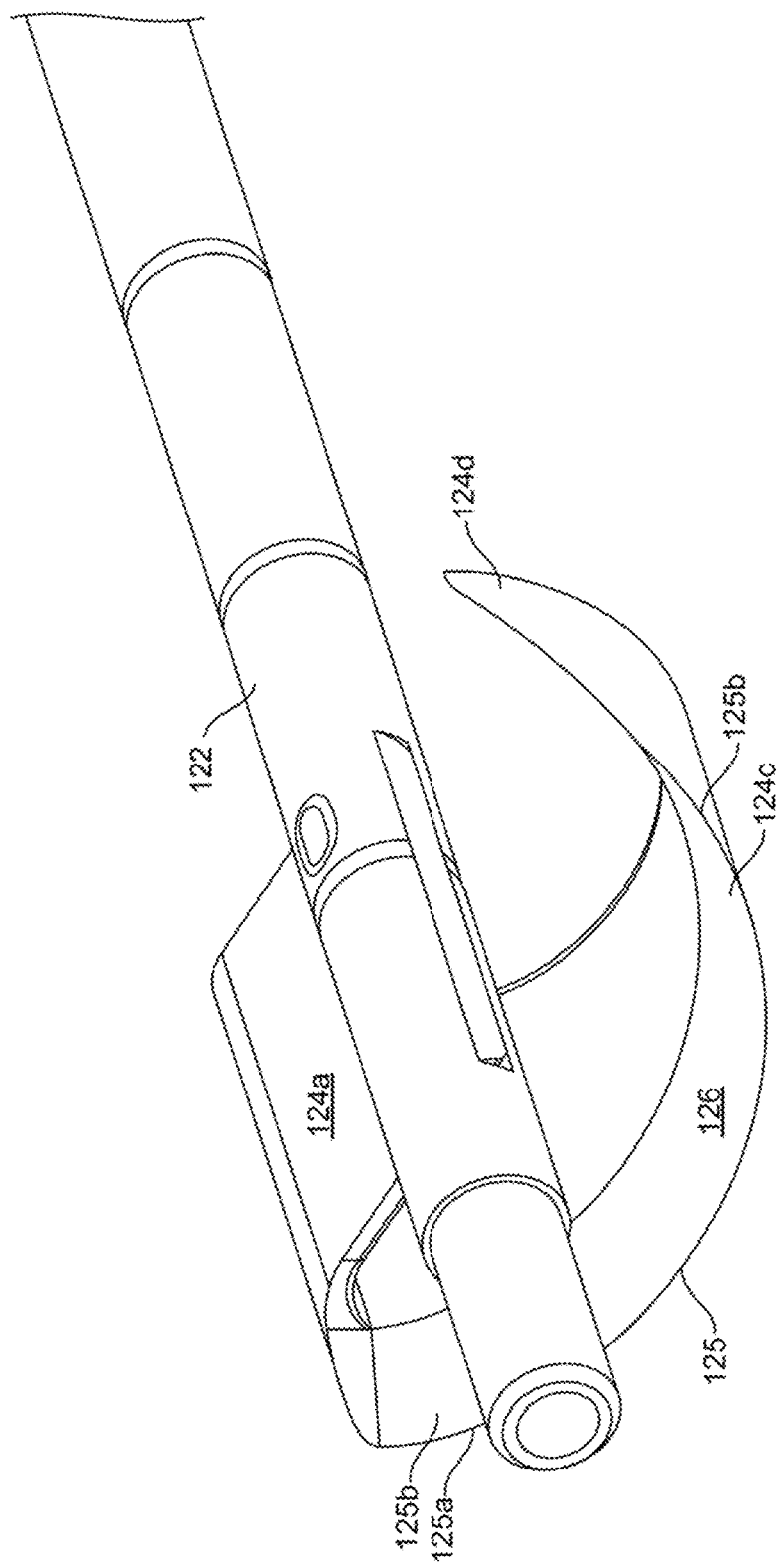
Figure 3A:
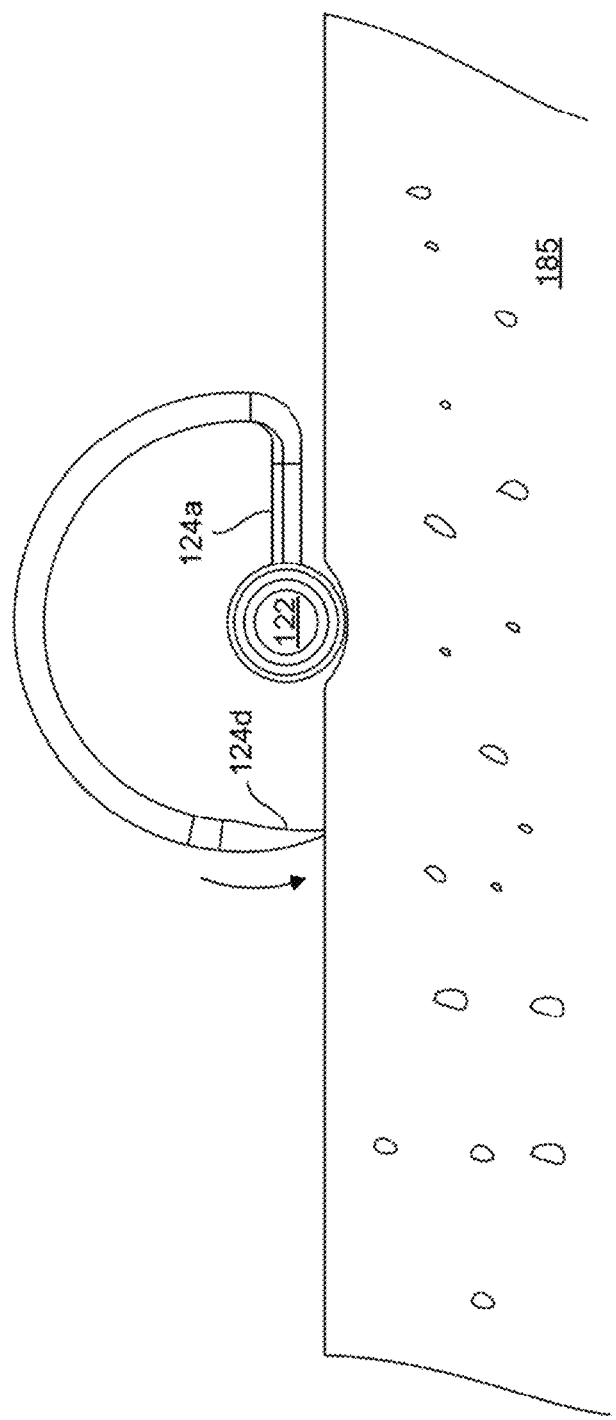
FIGS. 3A and 3B represent show end views of a cutting portion of a harvesting tool external to and the inserted into a QT respectively, in accordance with at least some embodiments.
Figure 3B:
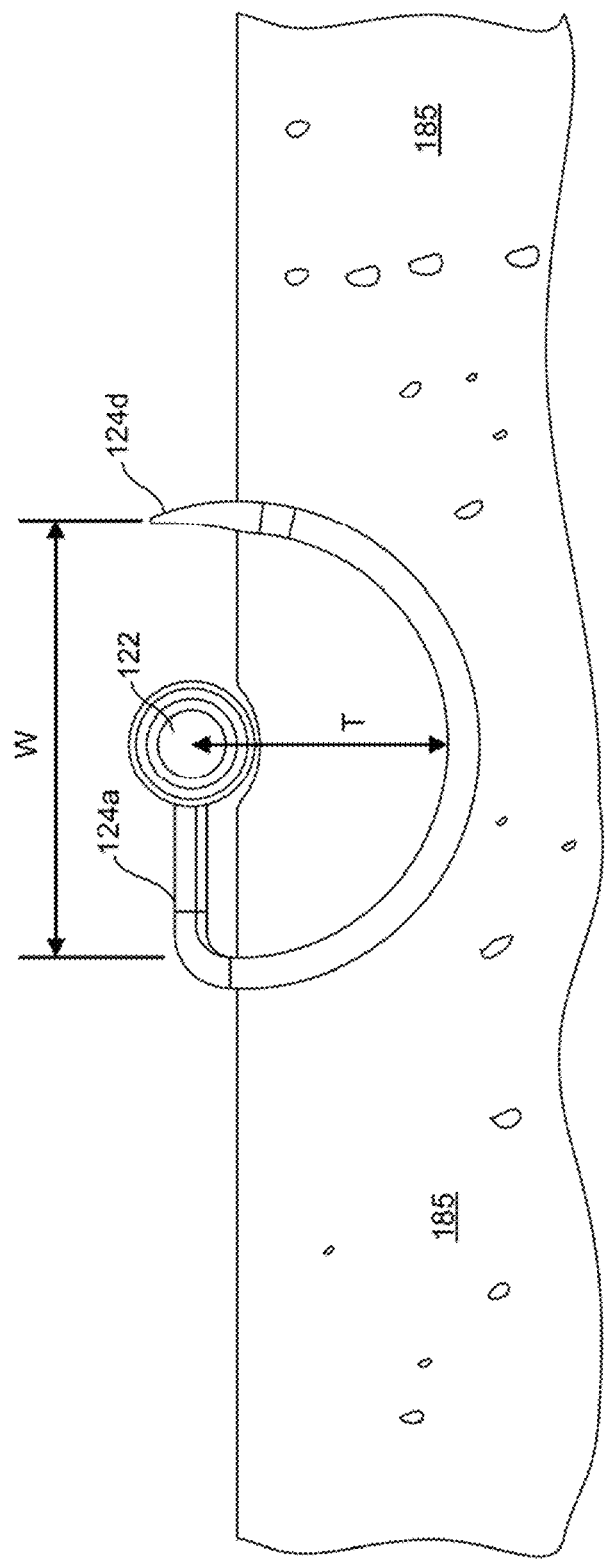
Figure 3C:
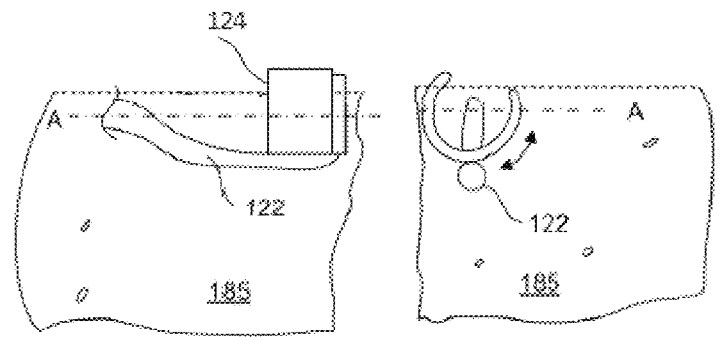
FIG. 3C schematically shows a side view and cross-section view of a cutting portion of a harvesting tool, in accordance with at least some embodiments.

Seen best in FIGS. 1A, 2A and 2B tendon harvester 120 generally includes a handle portion 121, a cutting portion 124 at the distal end and a shaft 122 therebetween. The shaft 122 may be configured to slide through opening such as opening 115 and operatively couple to guide such as guide 100 to maintain the offset "Z" from bar surface "A". In other embodiments the harvester may be used independently from a guide. The cutting or blade portion 124 may include a leading cutting edge 125 that is sharp or configured to cut through the QT along a length of leading edge 125, the leading edge defining a distal-most edge of cutting portion 124. In some embodiments this may be a proximal most edge and the cutting portion is pulled to form the graft. Best seen in FIG. 2B, an end view of harvester 120 and also FIG. 2C an isometric view, the cutting portion 124 may include a first portion 124a that extends radially away from the shaft 122 and may not include a cutting edge, followed by a semi-circular portion made up of arc 124b and arc 124c that partial encircles the shaft to form a partial or semi-circle or arced shape. Arc 124b and 124c may include cutting edges. A semi-circular cutting portion 124 will result in a matching semi-circular cross section of the QT graft having a graft thickness "T" and a width "W". The cutting portion 124 may extend around the shaft terminating with a piercing tip 124d. Tip 124d may have a tapered cross sectional thickness (FIG. 2A) and be tapered axially (FIG. 2A) at an angle β. As shown in FIGS. 3A and 3B the harvester 120 may initially be inserted adjacent the QT with the shaft 122 rotated such that the entire cutting portion 124 is on an anterior side of the QT, external to the QT. Rotation of shaft 122 may then rotate the cutting portion 124 and insert the tip 124d first into the QT following by the portion 124c, then 124b until portion 124a lies on an anterior surface of QT. In this inserted position, the QT may be sufficiently conformable to allow some of the shaft 122 to push into the anterior side of QT while portion 124a lies on anterior external surface of QT. In the inserted position, piercing tip 124d may extend back out of QT anterior surface and may be anteriorly spaced from cutting portion 124a.

In addition leading edge 125 of cutting portion 124 may be configured to pierce or cut through tissue while axially sliding or advancing the harvester. Leading edge 125 may include a tapered cross section or blade edge, the taper 126 shown best in FIG. 2C. Leading edge 125 may also define an angled leading edge relative to a longitudinal axis of the harvester, such that as the leading edge 125 extends around shaft 122 it also concomitantly axially extends further from an end of shaft 122 to form a circular helix leading edge. Angled leading edge 125 may extend at an acute angle Θ. (E.g. 20°-80°) Stated otherwise portion 124A defines a distal-most edge of cutting portion 124, closest to the end of shaft 122, and the edges 125a and 125b taper away from the end of shaft progressively. Leading edge angle or shape is configured to provide a gradual cutting during rotations introduction (as opposed to all at once) and to force tissue sliding relative to the cutting edge 125 during translation. Furthermore tip portion 124d may extend at a different angle β relative to edge 125b, so as to increase the angle of the leading edge 125 relative to the longitudinal axis L. During rotating insertion of cutting portion 124, the increase angle β is configured to aid initial penetration of tip 124d into the QT. Once in the inserted position the tip 124 including the portion up to point P and thereby the increased angle portion may be substantially external to the QT. Leading edge angle changes by the angle β (e.g. 5°-45° adjacent point P approximately disposed adjacent a lower surface 122a of shaft 121. Generally all angles are configured to ease cutting and rotational insertion of the cutting portion 124 into the QT 185. The cutting portion 124 may be semicircular shaped, rectangular shaped, U-shaped or V-shaped (U-shape shown in FIG. 2B), and a first leg or first side of the semicircular shaped, U-shaped or V-shaped cutting portion may define the first edge 125a and the second leg or second side of the semicircular shaped, rectangular shaped, U-shaped or V-shaped cutting portion may define the second edge 125b. The space between the sides of the semicircular shaped, U-shaped or V-shaped cutting portion is open allowing the harvested graft to pass therethrough. A top portion 124a spans at least a portion of the distance between the tops of the arms of the semicircular shaped, U-shaped or V-shaped cutting portion and helps keep the tendon cutting portion 124 positioned anteriorly relative to the QT. Stated otherwise, the top element 124a surfs the top/anterior surface of the QT.

With or without the guide, harvester 120 may first be inserted under the skin in an upwards facing first position, with the shaft 122 preferably anterior to and abutting an anterior surface of the QT 185 and the cutting portion 124 anteriorly disposed, as shown in FIG. 3A. The harvester 120 may then be rotated so as to insert the cutting portion 124 into the QT 185, shown in FIG. 3B. In the first position, shown in the FIG. 3A, the top portion 124a may lie on a first anterior surface portion of the QT and is rotated into the second position shown in FIG. 3B to be inserted into the QT. Top portion 124a is rotated so as to lie on a second anterior surface portion of the QT, laterally disposed relative to the first anterior surface portion, as the shaft 122 will rotate around an axis and remain approximately stationary or level relative to the QT 185. More specifically, top portion 124a has a first and second surface, on opposing sides of the top portion 124a, and in the first position, the first surface abuts a first QT anterior surface portion and in the second inserted position, the second surface of the top portion 128 abuts the second QT anterior surface portion located laterally from the first QT anterior surface. Embodiment 3C shows a side view and an end view of alternate cutting portion of a harvester 120. Shaft 122 may be bent or curved at the distal end so as to be attached to an alternate portion of cutting portion 124. Shaft 122 curves away from the axis A-A to couple to an underside of the cutting portion 124.

Figure 3D:
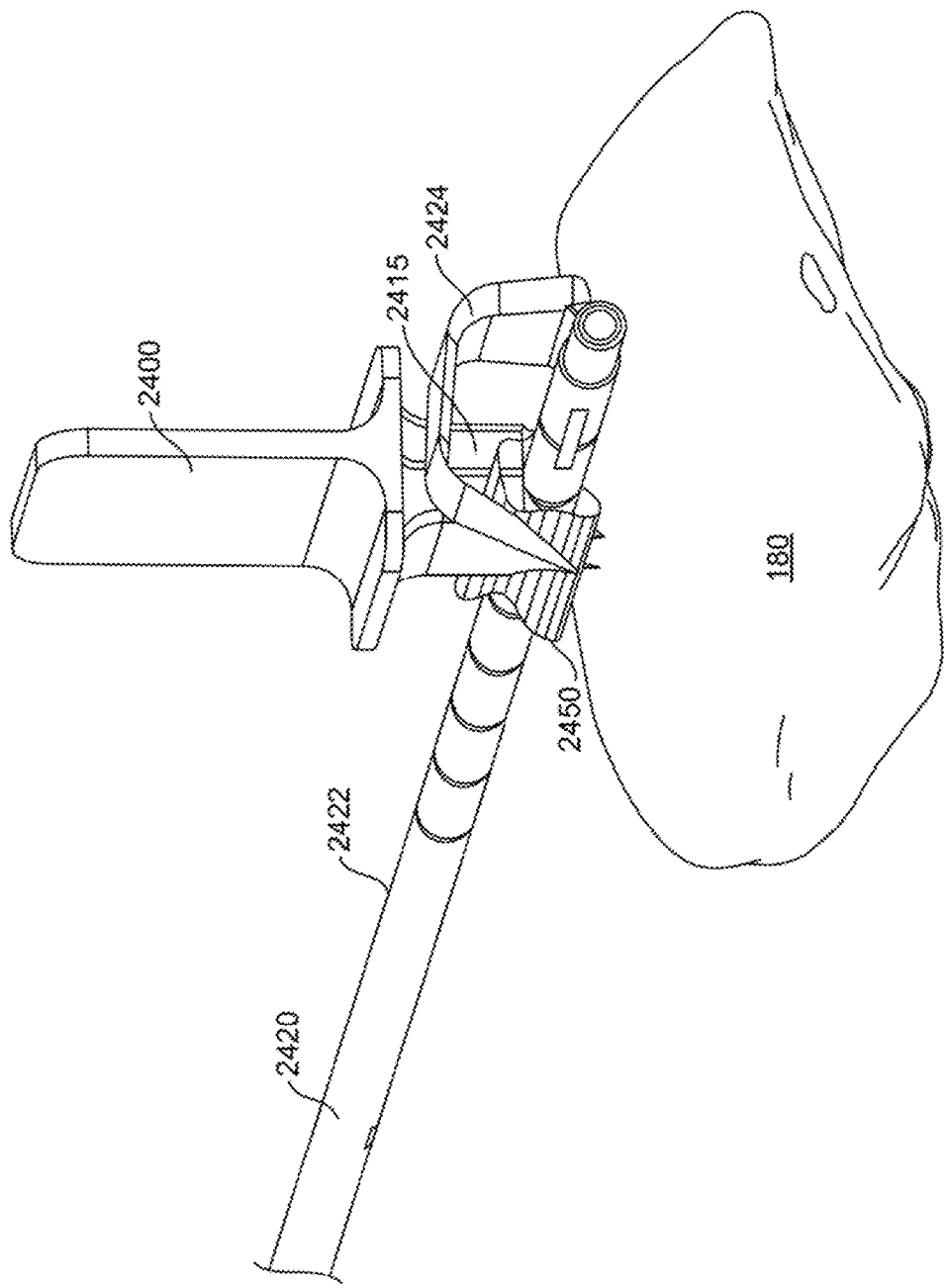
FIGS. 3D, 3E and 3F schematically show views of an exemplary cutting path of a cutting portion of a harvesting tool embodiment, in accordance with at least some embodiments.
Figure 3E:
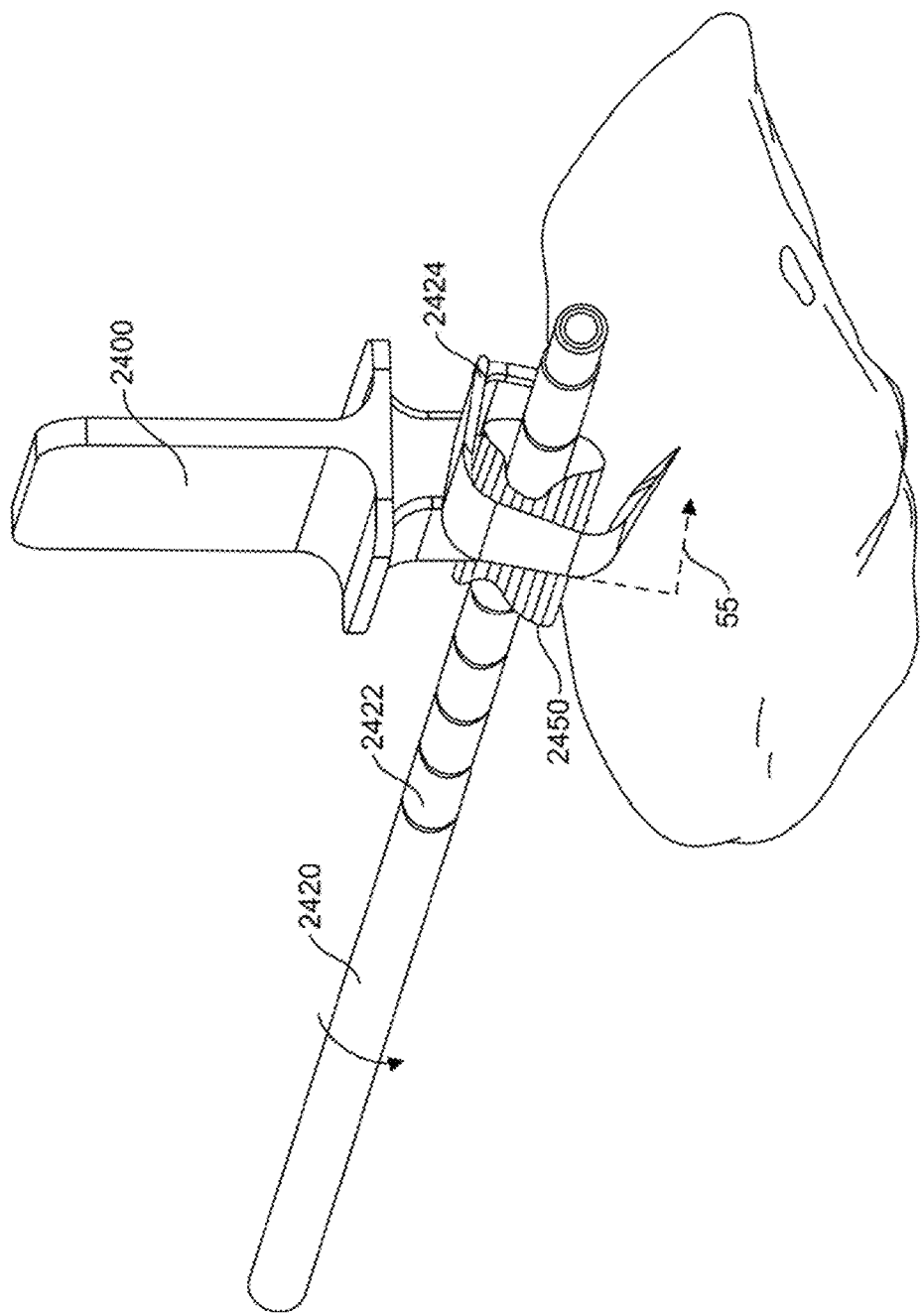
Figure 3F:
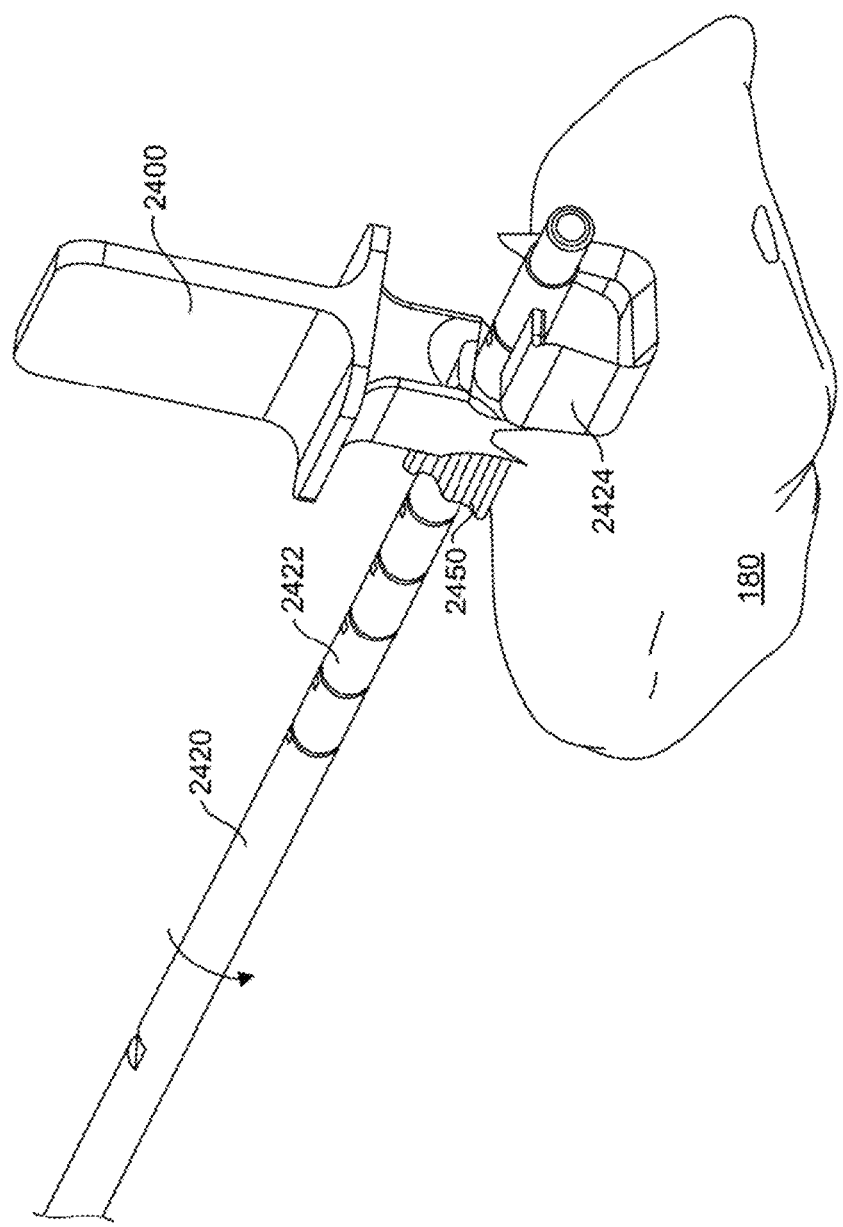

FIGS. 3D-3F disclose an alternative embodiment of either the keeper 2400 and or harvesting tool 2420, including an angular or cutting portion 2424. In these figures, the knee capsule and QT have been removed for clarity. Cutting portion 2424 is configured to form a polygonal cross section strip of tendon, such as a rectangle or square when rotatingly inserted therein. Therefore either the keeper 2400 or the harvester 2420 or both may include a cam portion 2450 having contoured surfaces configured to modify the motion of cutting portion 2424 to translate the rotation of the shaft 2422 and place the angular cutting portion 2424 into the QT and form an angular or polygon shaped cross section of graft, without tearing the QT. Shown in FIGS. 3D-3F are example cam portions 2450 coupled to shaft 2422. Keeper opening 2415 may also include surfaces that are contoured to cooperate with cam portion shown 2450. As the cutting portion 2424 is rotatingly inserted into the QT, cutting path 55 may therefore be defined by a combination of shape of cutting portion 2424, cam surface 2450 and keeper opening 2415 contours which may include another cam, and an exemplary path 55 is shown in FIGS. 3E and 3F. Stated alternatively, cam portion 2424 and keeper opening 2415 contours are configured to allow a cutting portion 2424 of a non-circular cross section introduced with a simple rotation movement to form a non-circular cross section graft.

Figures 4A, 4B:
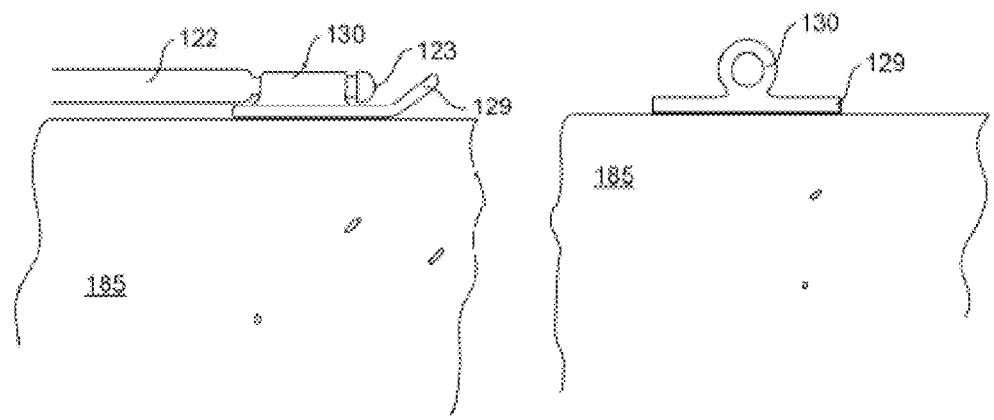
FIGS. 4A and 4B represent a side view and end view of a cutting portion of a harvesting tool having a surfboard, in accordance with at least some embodiments.

Further embodiments of harvesters 120 are shown in FIGS. 4A and 4B, including a surf element 129 that is rotatably independent of the cutting portion 124 (not shown) and shaft 122. The surf element 129 may remain rotationally stationary as the cutting portion 124 rotates between the first and second (inserted) position to be inserted into tissue. Surf element 129 may be coupled to the shaft 122 such that rotation of shaft 122 does not rotate the surf element 129, however translation of the shaft 122 may translate the top element 129. An example coupling may include a hollow shaft 130 extending from the surf element 129 and concentrically coupled to the harvester shaft 122, the hollow shaft 130 sized so as to easily slide around the harvester shaft 122. Harvester shaft 122 may terminate with a pin, or enlarged end 123 relative to the hollow shaft inner diameter supplying a means of retaining the hollow shaft 130 on the harvester shaft 122.

Figure 5C:
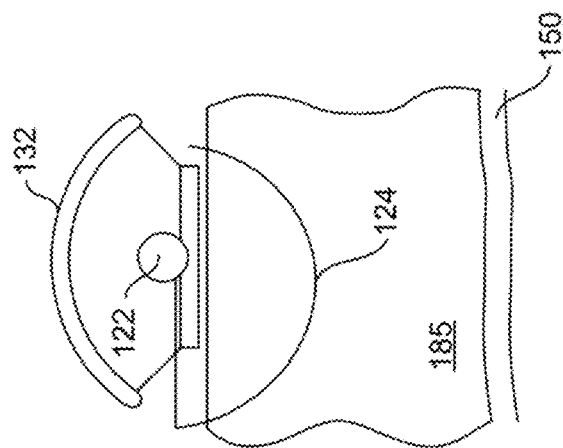
FIGS. 5A, 5B and 5C schematically show a side view, a cross-section view of a cutting portion of a harvesting tool in a first position and a cross-section view of a cutting portion of a harvesting tool in a second position respectively, in accordance with at least some embodiments.
Figure 5B:
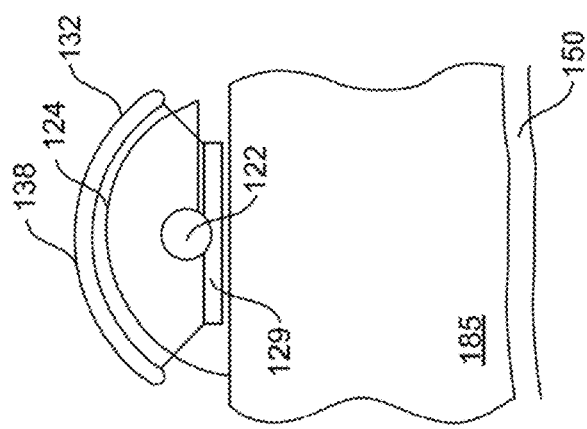
Figure 5A:
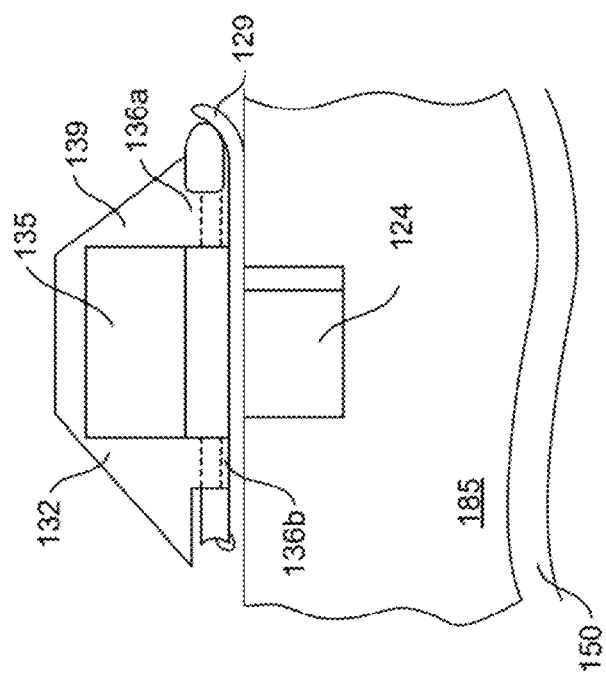

In further alternative embodiments a shroud 132 may be added to the distal end of harvester 120, shown FIGS. 5A, 5B and 5C. The shroud 132 is configured to protect anatomy from inadvertent damage by the cutting portion 124 while in the first (up) position. Shroud 132 is shown incorporated with the embodiment including the independent surf element or surfboard 129. Advantageously, and similar to the surf element 129, the shroud 132 remains stationary while the cutting portion 124 rotates into the tissue. Best seen in FIGS. 5A and 5B, shroud 132 may include a window 135 sized to enclose at least a portion of cutting portion 124. Shroud 132 may also be coupled to shaft 122 via at least one hollow shaft portion, similar to that described for the surf element 129. Shown in FIG. 5A are two hollow shaft portions 136a and 136b, disposed either side of the cutting portion, along the shaft 122. Shroud 132 may be a single piece construction including surf element 129. Best seen in FIG. 5B showing the cutting portion 124 in the first position, and recessed with shroud 132, shroud 132 may form a curved roof portion 138 so as to shield a substantial length of the semicircular or U shaped cutting portion 124, and more specifically to shield a substantial portion of the edge 125 of the cutting portion 124. As shaft 122 is rotated, cutting portion 124 rotates relative to the shroud 132 so as to emerge from the window 135 and into the target tissue 185. Window 135 is therefore sized to allow for passage of the cutting portion 124 in and out of the window 135. Front of shroud may be angled so as to form a more tapered tip, easing insertion of harvester 120 between the skin and anterior surface of QT.

Figure 6B:
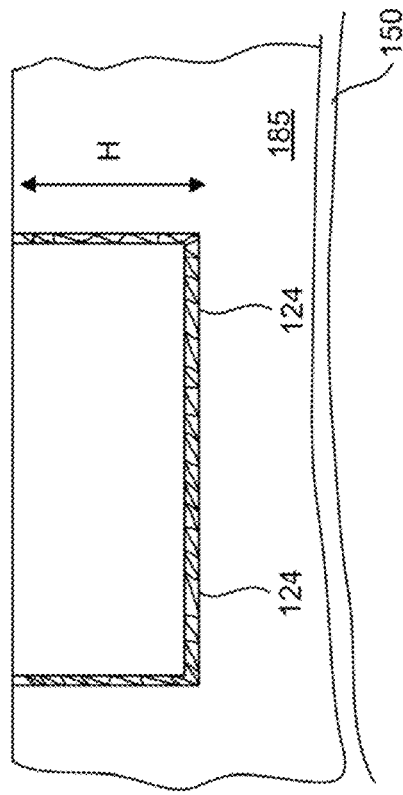
FIGS. 6A and 6B schematically show a cross section view of an alternative embodiment using a first and second cut of a cutting portion of a harvesting tool in a first and second position respectively, in accordance with at least some embodiments.
Figure 6A:
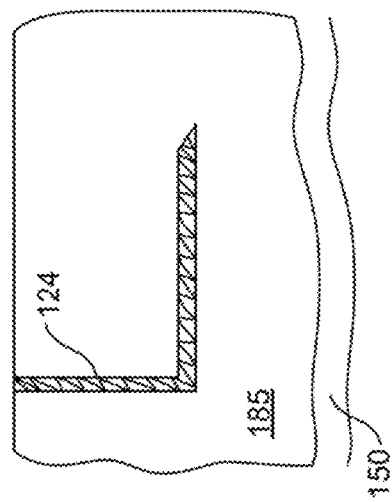

Alternative embodiments of the tendon harvester 120 may include a serrated edge 125 (not shown). Further alternatives for cutting portions 124 may be found in FIGS. 6A and 6B may include a two part cutter that has a cross-section in the form of an "L" that may require two passes along the QT. FIG. 6A shows the first pass into the QT 185, while FIG. 6B shows the first and second pass. This may be advantageous in the case of a shallow QT, where a circular or deep graft is not achievable. In order to harvest sufficient cross-section of QT, a wide graft may be alternatively obtained with two cuts, mirror image from each other, rather than a more circular cross section as shown in FIG. 2B. The inventor also envisions using any of the aforementioned tendon cutter 120 embodiments after at least one vertical cut along a QT has been formed. The at least one vertical cut can be formed using a standard means such as a Quad Tendon Graft Cutting Guide, known in the art. Once the at least one vertical cut has been formed, the aforementioned embodiments may be manipulated to lie within at least a portion of the at least one vertical cut and strip a length of tendon, the at least one vertical cut aiding the harvester 120 in penetrating the QT. The Quad tendon Graft Cutting Guide may form two parallel vertical cuts at selectable distances from each other.

Figure 7A:
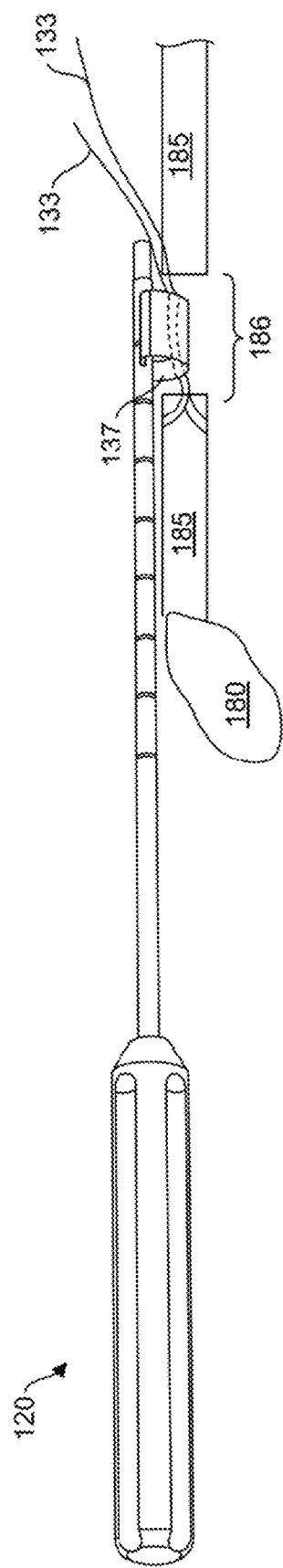
FIGS. 7A and 7B schematically show a side view and an end view respectively of a cutting portion of a harvesting tool with an enclosed cutting portion, in accordance with at least some embodiments.
Figure 7B:
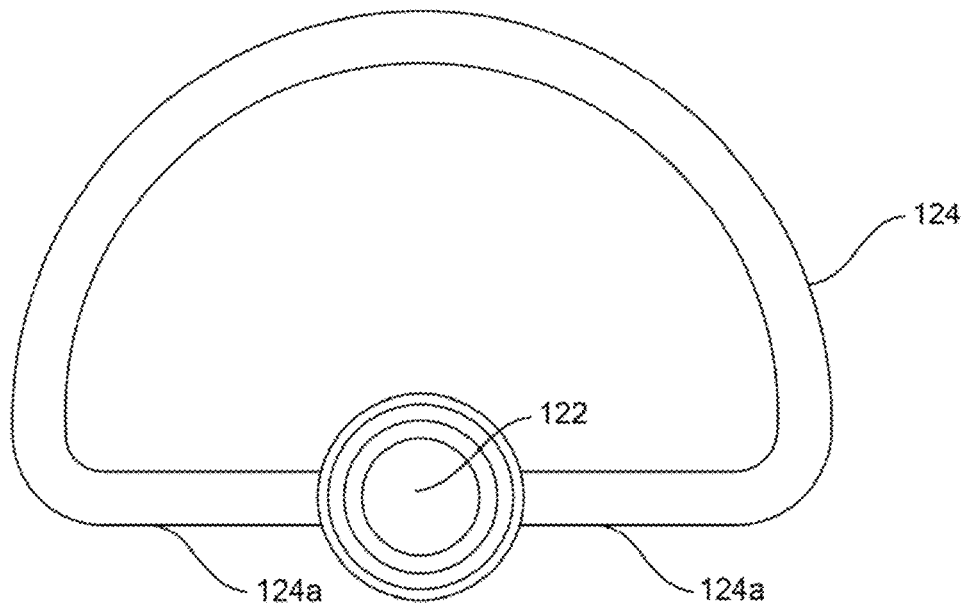

FIGS. 7A and 7B show a further embodiment including a fully enclosed cutting portion 124 (best seen in FIG. 7B). Stated otherwise, the top portion 124a extends all the way across the semi-circular, rectangular, U or V shaped cutting portion 124. This embodiment would require a skin incision 186 to be prepared before inserting the enclosed cutting portion 124 over the proximal or distal QT. Advantageously, the point of insert may then be spaced away from the patella 180 and the harvester 120 may be retracted, pulled or manipulated towards the patella 180 to harvest the QT graft. This method would preferably include first creating an opening 186 in the QT and attaching a traction member such as threading a suture 133 through a first end of the QT. Suture 133 may then be threaded through a portion of the harvester 120, and may be threaded through the cutting portion 124 so as to draw the QT toward the cutting portion 124. Alternatively, the traction member may be a soft tissue grasper instrument. Of note, cutting portion cutting edge may preferably be on one side 137 of cutting portion 124 but could be on either or both surfaces.

Once QT end is disposed at least partially within cutting portion 124, or butted up against the QT end, harvester 120 is withdrawn to as to strip a portion of QT 185 and provide a QT graft.

Visualization

Figure 8A:
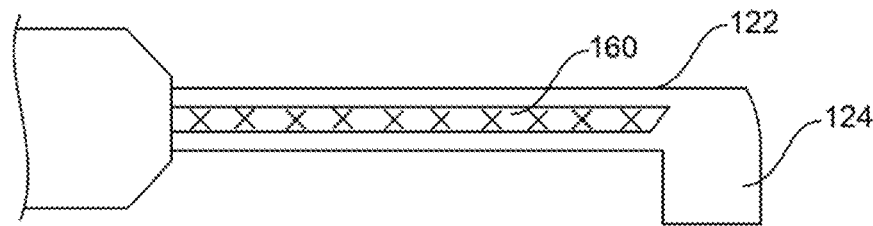
FIGS. 8A and 8B show a side view and a cross-section view of a harvesting tool with a scope concentrically disposed, in accordance with at least some embodiments.
Figure 8B:
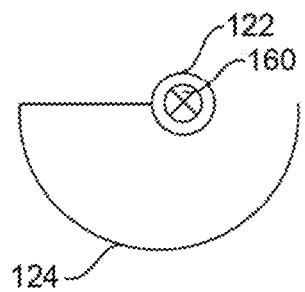
Figure 8C:
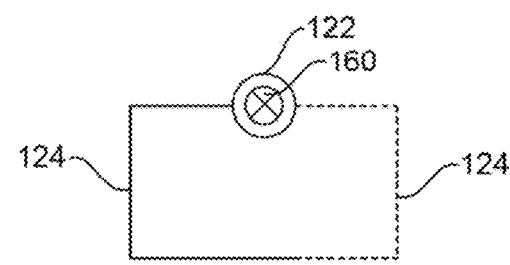
FIG. 8C schematically shows a cross-section view of an "U" shaped cutting portion, with a scope centrally disposed, in accordance with at least some embodiments.

Seen in FIG. 8A, harvester 120 may incorporate visualization means selectively coupled to the QT system. Visualization may allow the user to adjust the depth of cut and trajectory of the cutting portion 124 in real time. An exemplary embodiment may therefore include a scope 160, such as an arthroscope, selectively coupled to a distal portion of the harvester 120, including any of the harvester embodiments disclosed heretoforth. Shown in FIG. 8A is a scope 160 concentric with the shaft 122. Shaft 122 is hollow so as to receive scope 160. FIG. 8B shows an embodiment with a semi-circular or U shaped cutting portion 124. Scope 160 may be coupled to shaft 122 so that scope 160 rotates with shaft 122 as cutting portion 124 is move to the second position. Alternatively scope 160 may be inserted into shaft 122 so as to remain stationary while shaft rotates to control the cutting portion 124. FIG. 8C shows a scope 160 associated with the "L" shaped cutter, having been applied twice, (second time dashed lines) the second time in a mirror image position. FIG. 8C could also be achieved using a rectangular shaped cutter, applied once.

Figure 9A:
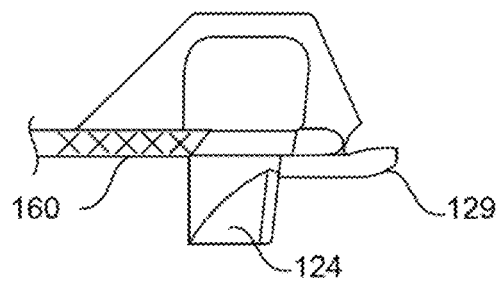
FIGS. 9A, 9B and 9C schematically show a side view, a cross-section view of a cutting portion of a harvesting tool in a first position and a cross-section view of a cutting portion of a harvesting tool in a second position with a scope, in accordance with at least some embodiments.
Figures 9B, 9C:
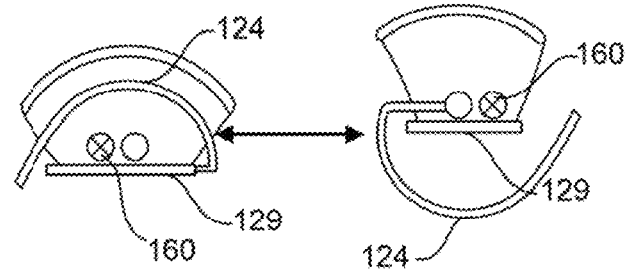

Alternatively scope 160 may be coupled directly adjacent shaft 122. FIG. 9A shows an embodiment wherein the scope 160 is coupled along an outer surface of shaft 122 and terminates near a first end of shroud window 135, so as to prevent interference between the scope 160 and cutting portion 124 during rotation of the cutting portion 124. More specifically, scope 160 may terminate so that the scope tip is spaced away from the trajectory of rotation of the cutting portion 124, so that rotation of the cutting portion to and from the second position does not interfere with the scope tip. FIG. 9B is a representation of the position of the scope 160 relative to shaft 122 and cutting portion 124 in the first position where the cutting portion 124 is substantially within the shroud 132. In this figure, surf element 129 and scope 160 are shown for reference of location, but may not be present in a true cross section of shaft 122 including the cutting portion 124. FIG. 9C shows a representation of the position of the scope 160 relative to the shaft 122 in the second position, with the cutting portion 124 within tissue. Again the scope 160 and surf element 129 are shown for convenience of discussion, as reference elements only. The scope 160 is coupled so as to rotate with the shaft 122. FIGS. 10A-10C show an embodiment where the arthroscope 160 remains stationary, while the cutting portion 124 rotates. The scope 160 is shown disposed on an anterior side of shaft 122, and terminates proximally relative to the cutting portion 124, so as to allow cutting portion 124 to rotate and emerge from shroud 132. FIGS. 10B and 10C are cross sectional representations of the scope relative to the shaft 122 and shroud 132, with the surf element 129 and scope 160 included as reference elements to show their relative position. The inventors envision that a scope 160 may be positioned in many alternative places relative to the harvester 120, so as to aid in visualizing the tissue surrounding the harvester 120, such as inferior to the shaft 122 or above the shroud roof portion 138. Other embodiments (not shown) include an alternative embodiments where the scope 160 may be selectively retractable while cutting portion 124 is rotating, and then return to a more distal location thereafter, towards the tip of shaft 122. This may allow scope to be closer to cutting edge 125 of cutting portion, and improve visualization.

Bone Plug Harvesting

Figure 11B:
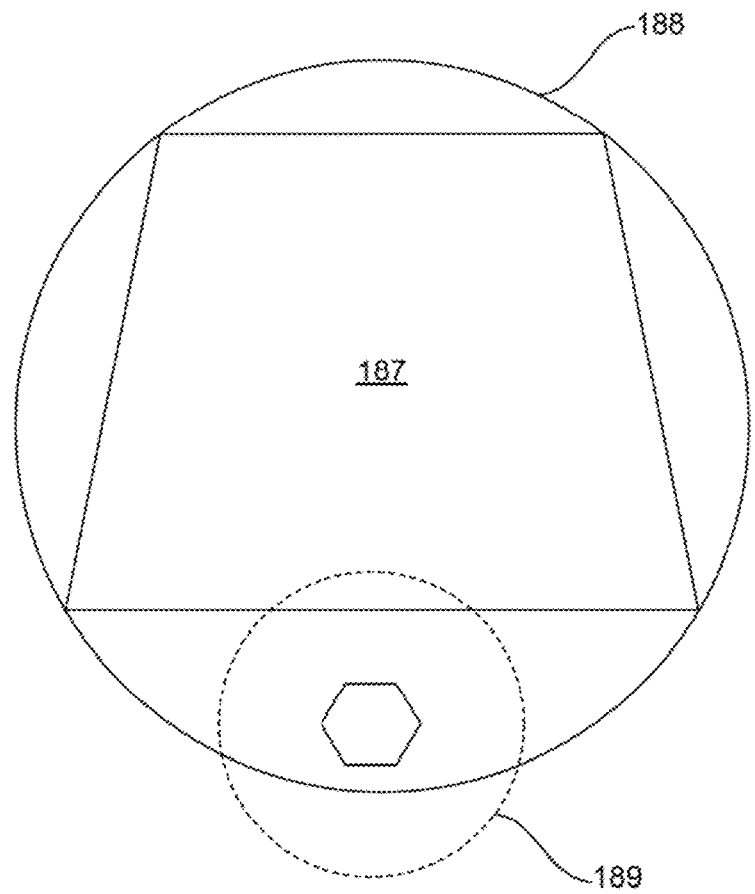
FIG. 11B shows a cross section of a bone block inserted in a round cross section hole, according to existing prior art.

Shown in FIG. 11A is a representation of a known means of harvesting a portion of the patella 180 that is attached to the QT 185. Traditionally bone blocks have been harvested by making 2 vertical sagittal saw cuts 175a and 175b, using a sagittal saw 190, followed by a bottom cut 195 with an osteotome 196. The resulting bone block 187, shown in FIG. 11B is generally angular, such as rectangular, which then is fixed within a round drill hole 188 with a round interference screw 189. The sharper corners of the bone block 187 may cause insufficient bone-bone ingrowth and may also increase the likelihood of fractures in the remaining patella 180.

Figure 12A:
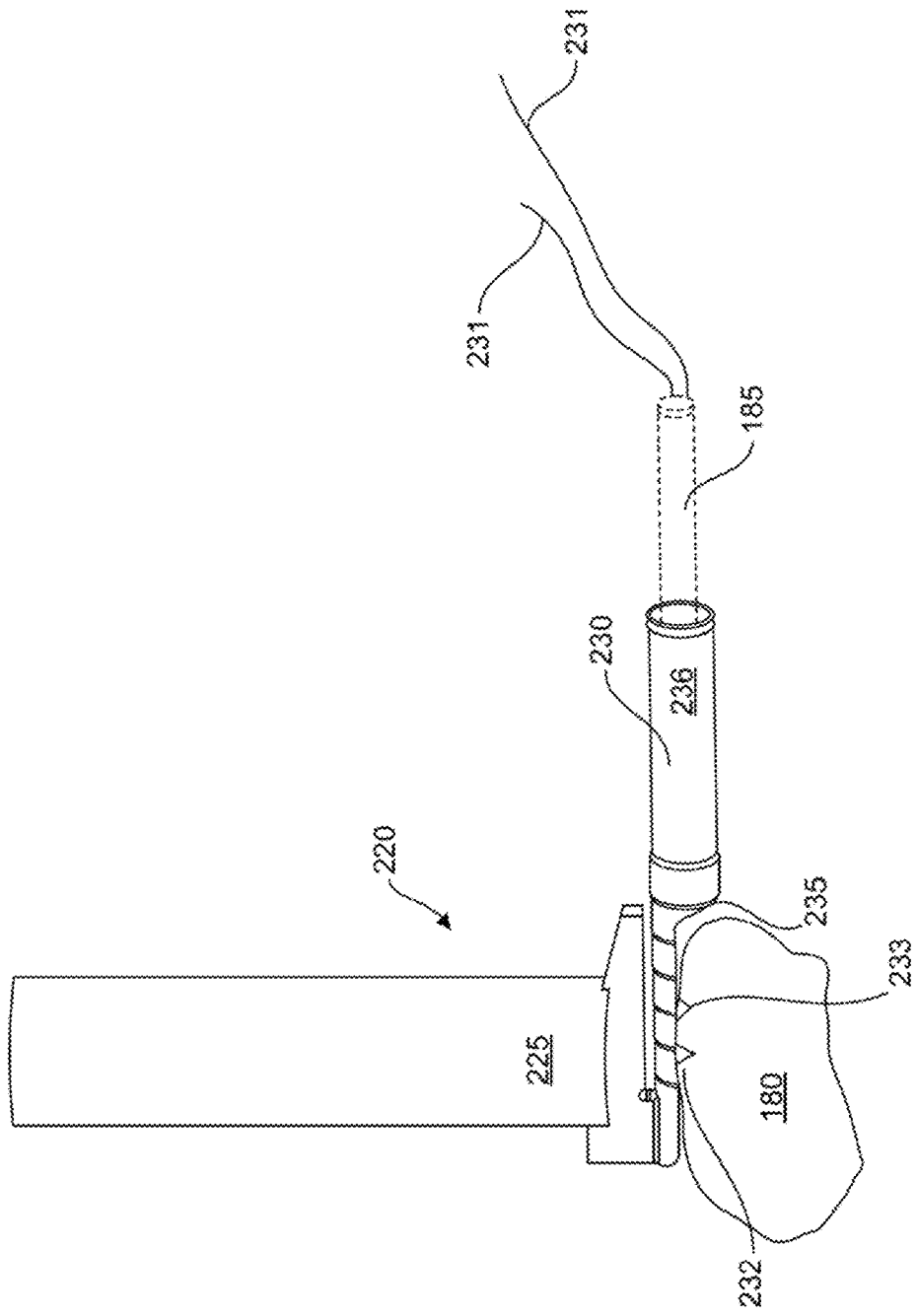
FIGS. 12A-H schematically shows a system and method of forming a rounded bone block using a trephine, in accordance with at least some embodiments.
Figure 12B:
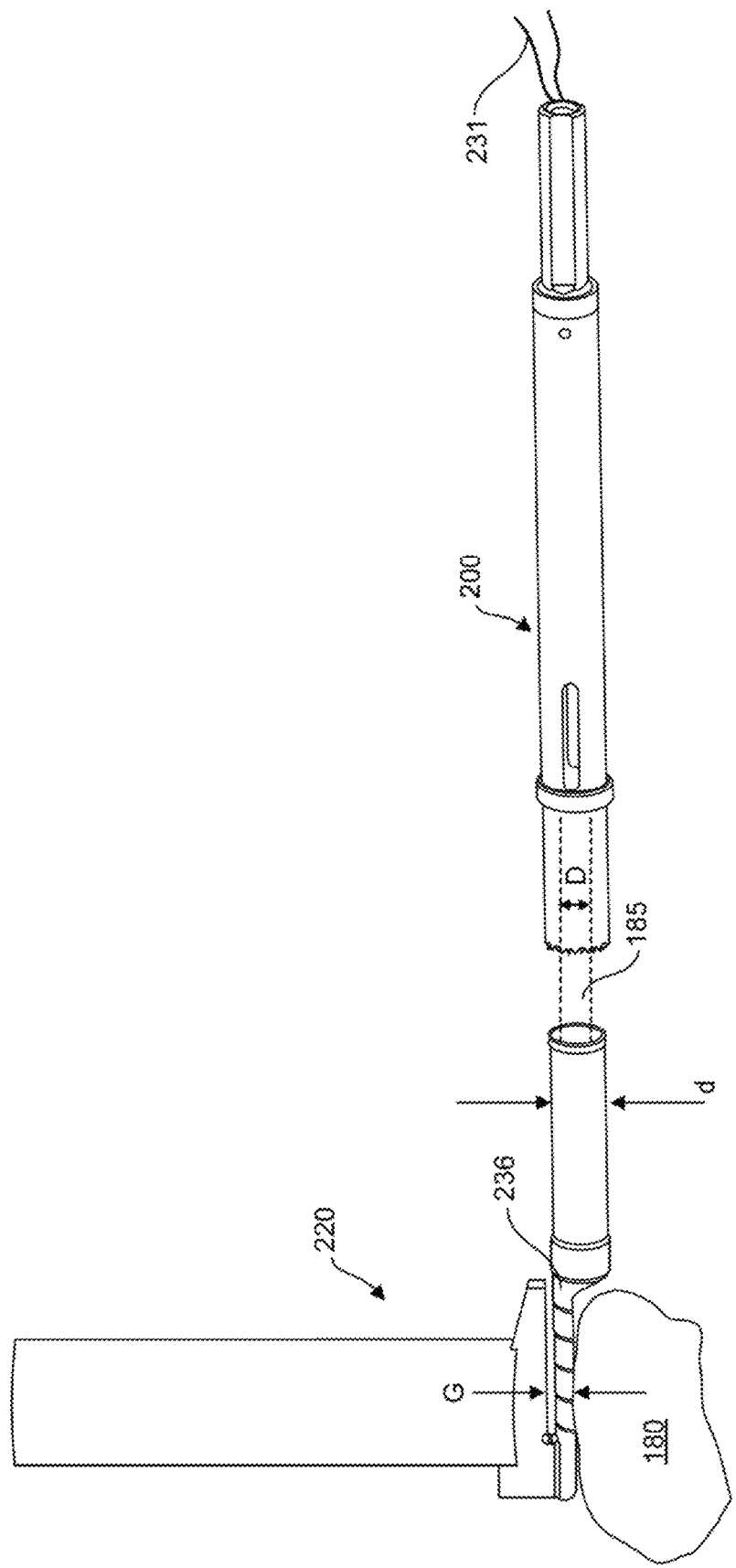
Figure 12C:
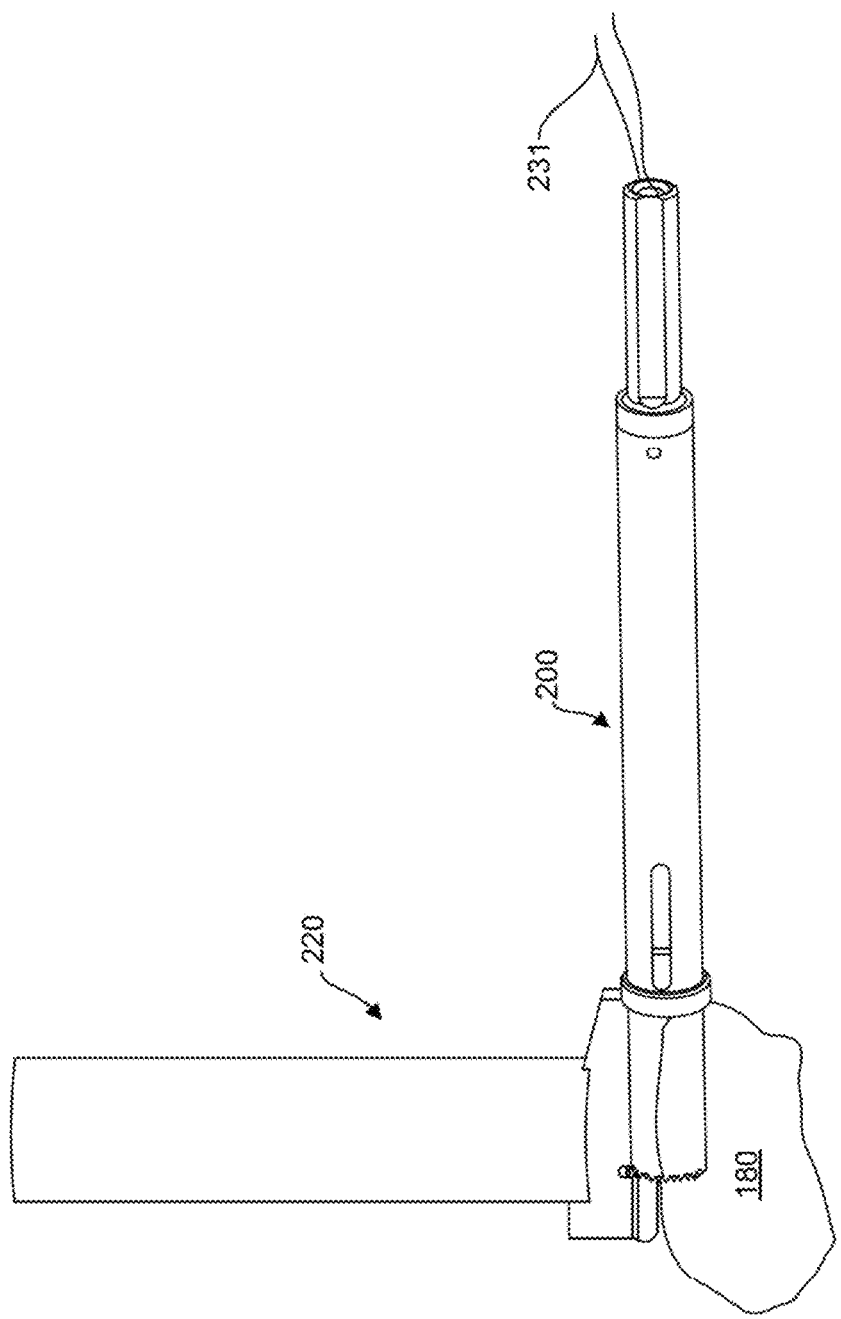

FIG. 12A-H show a system and method to produce a rounded cross-section bone block, to potentially improve bone-bone ingrowth with the round drill hole 188 including a trephine 200 and an aligner 220. Trephine 20 may be rotated so as to cut the bone, using a motorized drill (not shown) that may be coupled to an end of trephine 200. The system may also produce a rounded harvest defect in the remaining patella 180 reducing potential fractures. The trephine 200 defines a drill with a hollow core, for removing a rounded portion of the patella 180. The aligner 220 is configured to maintain the trephine 200 on track, to prevent diversion as the trephine 200 advances; the aligner 220 sets depth, trajectory and stroke length for the trephine 200. As such, aligner 220 has a handle 225 and a cylindrical shaft 230. The cylindrical shaft 230 may have a lumen therethrough with a diameter sized to fit around a harvested portion of QT 185. In some embodiments, to allow the largest possible cross section of the harvested portion of QT 185 to fit within the lumen, a portion of the cylindrical shaft 230 may be eliminated along its whole length yet leaving enough remaining to still provide guidance to the trephine 200. For example the posterior ⅓ of the circumference may be removed along the entire length of shaft 230. In a further alternative embodiment shaft 230 diameter, or effective diameter if the lumen of the shaft 230 is only a partial circumference, may be larger than trephine diameter and trephine may extend within the shaft. Stated otherwise an inner lumen surface of shaft 230 may guide the trephine translation. As shown in FIG. 12A, cylindrical shaft 230 includes an angled or contoured open first end 235 configured to engage a surface of the patella 180 and aid in aligning the aligner 220 and thereby trephine 200. Aligner 220 also includes a posterior surface 232, configured to rest on the patella 180 and may further include a series of spikes, teeth or protrusions 233 to aid in gripping or engaging the patella surface. Surface 232 and 235 may be continuous with each other to form an opening along a length of the cylindrical shaft 230 to receive an anterior portion of the patella 180. Opening and thereby surface 232 and 235 may define a reference surface for resting on an outer surface of patella, defining pathway for trephine 200. The method may therefore include at least partially stripping a portion of the QT 185 rendering a partial QT graft, still coupled to the patella and threading suture 231 through a free end of the partial QT graft. Free end of the QT 185 may then be slid through the cylindrical shaft 230, and the aligner 220 first surface 235 placed to abut an end surface of the patella 180 and the aligner posterior surface 232 placed to abut an anterior portion of the patella 180. The cylindrical shaft 230 is further configured to cooperate with the trephine 200 such that the trephine 200 may rotate and translate along QT 185 and patella 180 and also rotate and translate along an outer surface of cylindrical shaft 230, as shown in FIGS. 12B and 12C. Cylindrical shaft 230 guides the trephine 200 along a preferred track. As such cylindrical shaft 230 may have an outer diameter "d" smaller than inner diameter "D" of trephine 200, however configured to allow rotation of trephine 200 while still limiting the path of the trephine 200 to as to control the depth and trajectory of the trephine 200 towards and into the patella 180. Posterior surface 232 may be adjustable, or the teeth 233 may be removable so as to adjust the bone block thickness, adjusting for different anatomy, graft height and trephines. FIG. 12C schematically shows the trephine 200 advanced so as to form a first cut along the patella. In this position, trephine 200 covers outer surface 236 of aligner including reference surfaces 232 and 235 disposed directly adjacent handle 225. As can be seen, gap "G" between handle 225 and outer surface 236 is sufficient to receive a thickness of trephine 200 and allow passage of trephine 200 into the patella 180. Outer surface 236 should also be configured so as to allow easy advancement of the trephine 200. Outer surface 236 may be cylindrical and equivalent to or continuous with cylindrical portion "d". In one form aligner 220 may include a single continuous cylinder with a portion removed configured to abut against a portion of patella 180, the portion removed forming the posterior surface 232 and contoured end 235.

In some embodiments a motorized drill (not shown) may be parallel or perpendicular to trephine 200 and offset to the trephine. A variety of gears or flex drives may help operatively couple the trephine and motorized drill. In order to ensure the aligner 220 is not moved by the trephine 200, a flexing joint may be placed between the trephine 200 and the motorized drill. Such a flexing joint may transmit torque and compression but not angular misalignment. E.g. a spring connection. The motorized drill may be positioned proximal to or distal to the trephine 200.

Figure 12D:
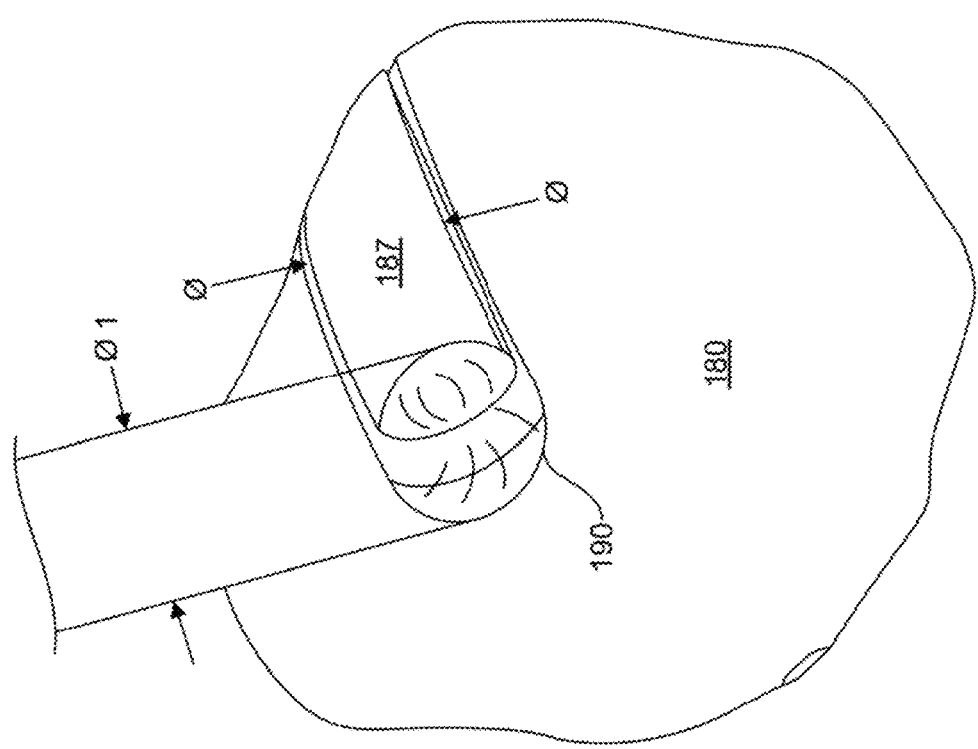
Figure 12E:
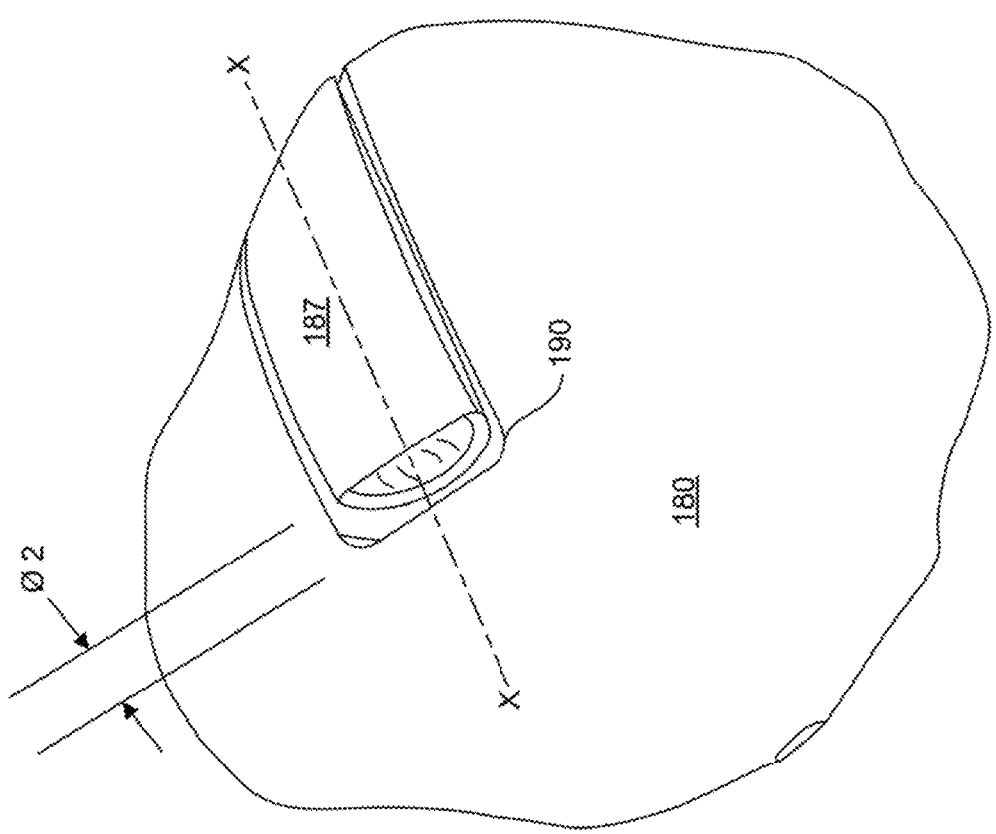
Figure 12F:
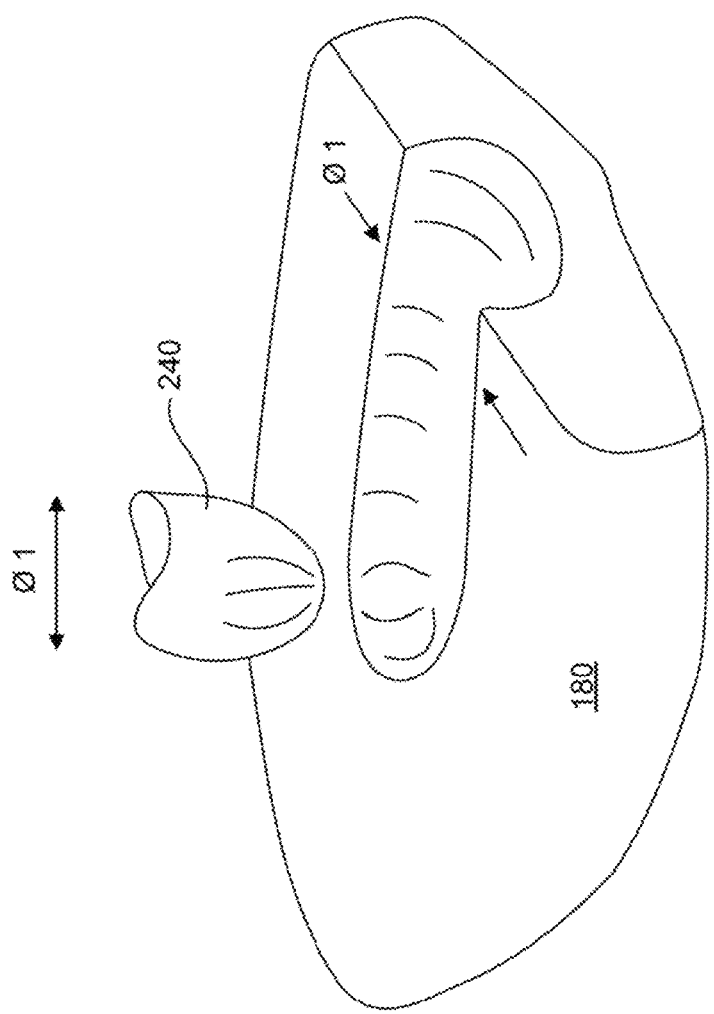

As shown in FIGS. 12D and 12E, an example bone block 187 is shown. Aligner 220 and trephine 200 are configured so as to form a bone block 187 from an anterior portion of patella 180, including the anterior outer surface of patella 180. The trephine 200 may rotate and translate simultaneously or may initially translate or slide along a portion of the QT and then rotate so as to cut into the patella 180 and form the bone block 187. The method of preparing a round cross-section patella bone block 187 may further include terminating the bone block 187 using a spherical drill 240. FIGS. 12D and 12E represent various embodiments of resulting ends 190 of the remaining patella. Once trephine 200 has cut a portion of the patella 180, a spherical drill 240 represented in FIG. 12F with bone block 187 removed for clarity may be oriented approximately perpendicular to an end 190 of the bone block 187 (cut portion formed by trephine 200) and applied so as to round off the edges of cavity in remaining patella 180. This is simultaneously release the bone block 187 from the patella and form a rounded cavity end 190. This may reduce likelihood of cracking or fractures at corners of patella 180. Spherical drill 240 may have a diameter Ø1 that is approximately equivalent to a resulting bone block diameter Ø, represented in FIG. 12D. In an alternative embodiment that may save some patella tissue a spherical drill 240 be a diameter Ø2 substantially smaller than Ø1, and potentially half that of bone block diameter Ø, represented in FIG. 12E. This spherical drill 240 may then be inserted into two locations, directly adjacent each other, or simply rotated around a long axis X-X of bone block 187. This sweeps a spherical cut with minimal bone loss.

Figure 12G:
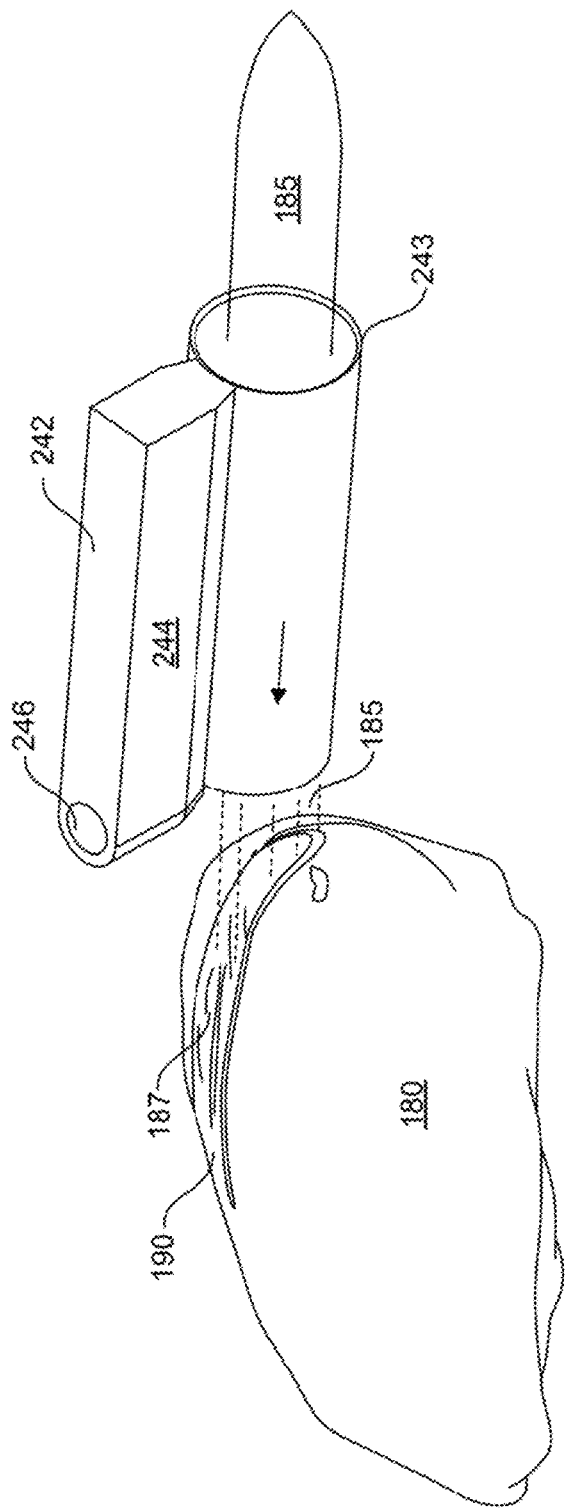
Figure 12H:
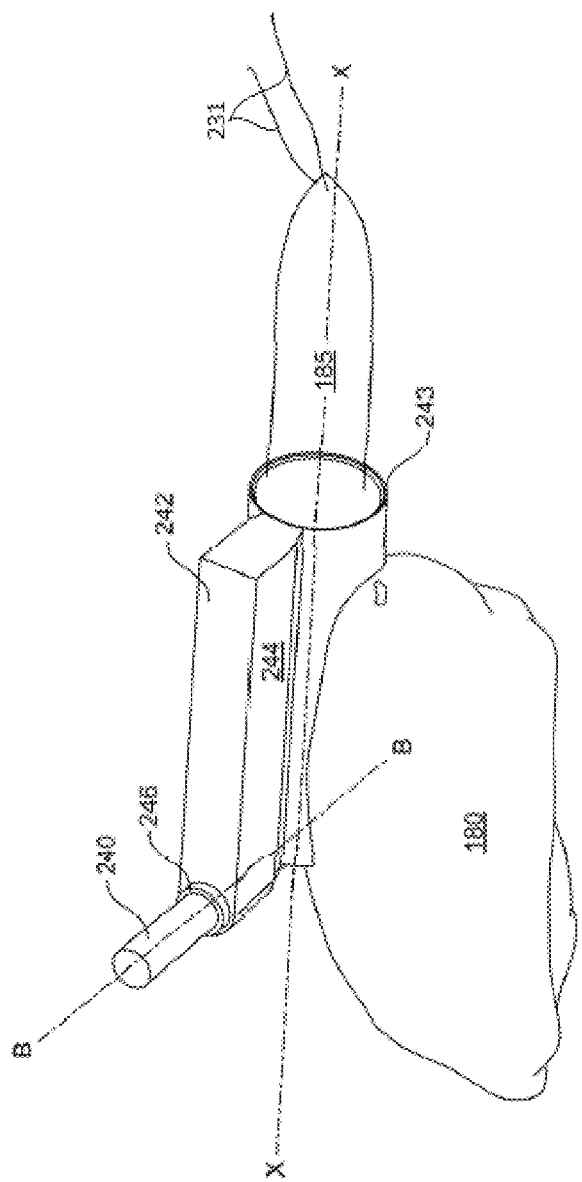

A method of controlling the spherical drill 240 is represented in FIGS. 12G and 12H, using a rotary end cut guide 242. As shown trephine 200 and aligner 220 may be removed resulting in a QT graft 185 and partially cut bone block 187, the bone block may still be attached at an end 190. Guide 242 may include cylindrical portion 243 configured to slide over QT graft and in between still coupled bone block 187 and patella 180. Handle 244 may aid in sliding the guide 242. Once cylindrical portion 243 is disposed substantially along the bone block 187, so as to abut the coupled end 190 of bone block 187 within patella 180, a spherical drill 240 may be used to disconnect the bone block 187 and form a rounded end within the patella 180. Handle 244 may include an opening 246 for receiving a spherical drill 240, seen best in FIG. 12H. Opening 246 defines a long axis B-B that is perpendicular and intersecting axis X-X and disposed so that at least a portion of opening extends beyond cylindrical portion, allowing the spherical drill 240 passage into the patella 180 at the still coupled end of bone block 187. A portion of opening 246 may overlap cylindrical portion 243 so that tissue removed by spherical drill 240 is continuous with bone block 187. Such position is best represented in FIGS. 12D and 12E. If a spherical drill 240 with a smaller diameter than bone block is utilized, guide 242 may be rotated around axis X-X during drilling to form a rounded end in the patella 180, reducing stresses as described herein. In this case opening 246 may have a diameter sized to receive spherical drill 240, but the size or diameter may be selectable or adjustable depending on drill diameter choice. Opening 246 may also have a stop associated with it, configured to limit the depth of cut of the spherical drill 240 to approximately the same depth as the bone block 187.

Double Bone Block Harvesting

Figure 13A:
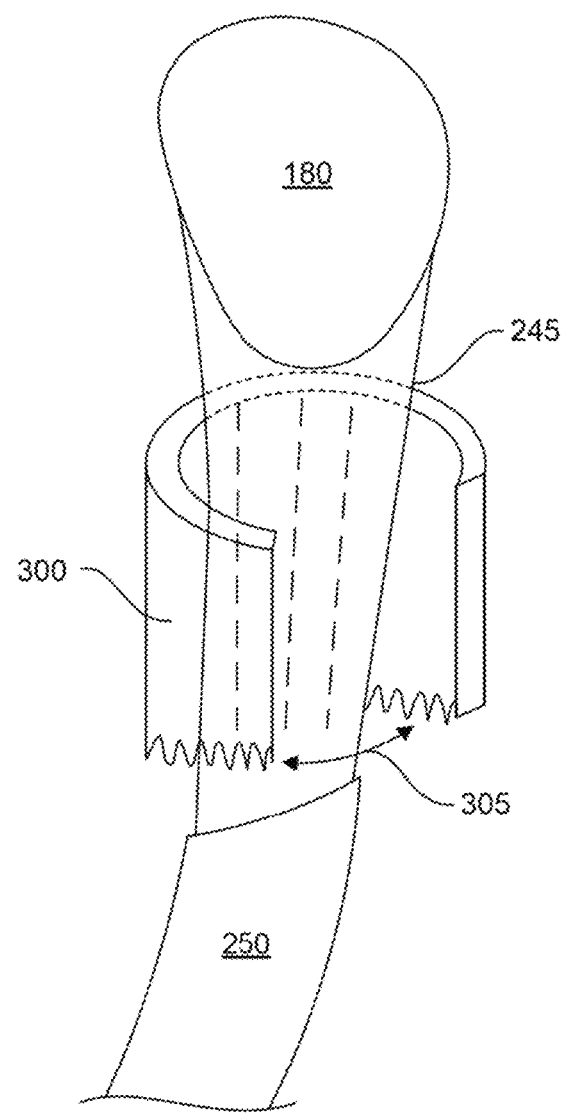
FIGS. 13A-D schematically show a system and method of forming two round bone blocks using a trephine, in accordance with at least some embodiments.
Figure 13B:
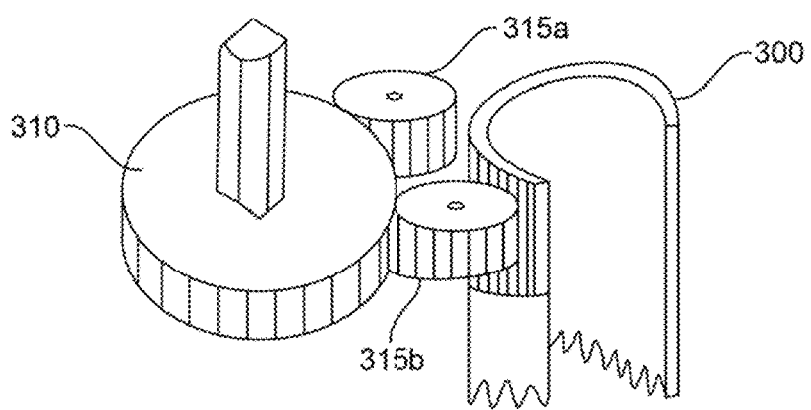
Figure 13C:
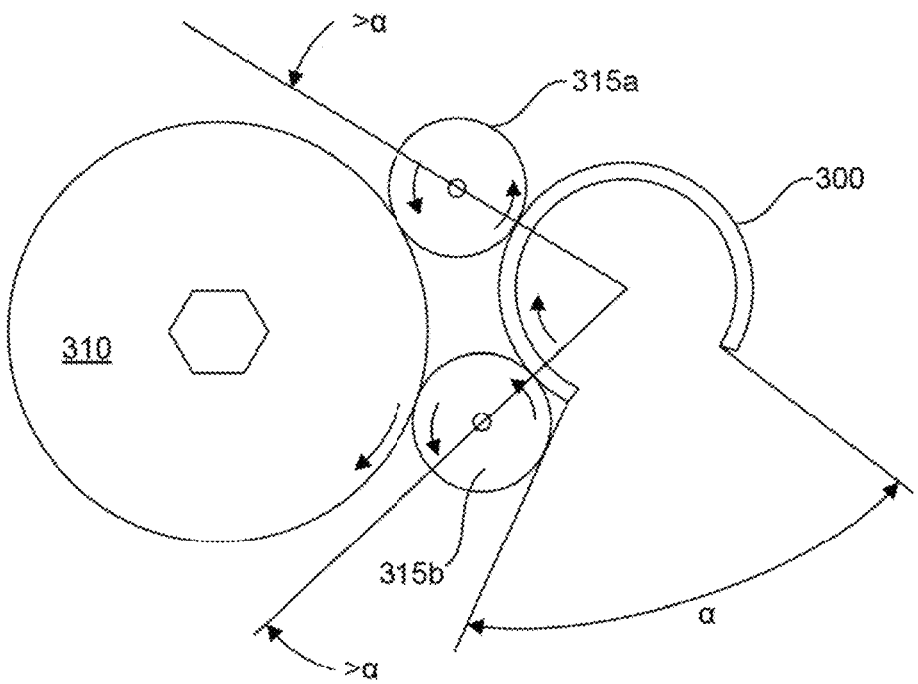
Figure 13D:
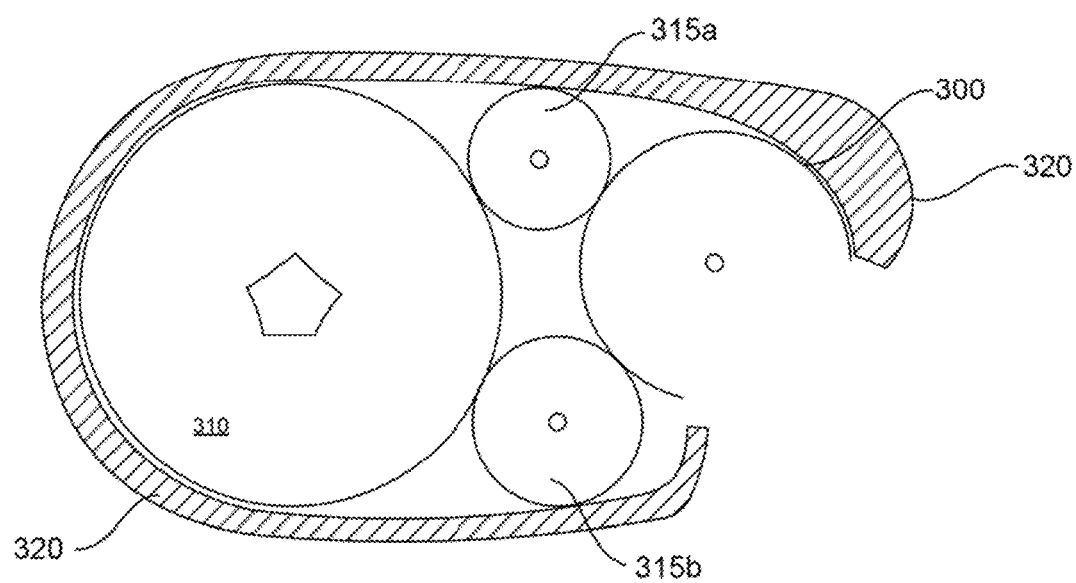

In some cases a double bone block harvest is preferred, wherein the patella tendon 245 is harvested, the patella tendon 245 extending between the patella 180 and the tibia (tuberosity) 250. As schematically shown in FIG. 13A-D, a trephine embodiment is disclosed for obtaining a bone block from both the patella 180 and tibia 250. This presents a unique situation in that the tendon 245 is continuous and so an end of a tendon may not be readily available to insert into the trephine as described in FIGS. 12A-12E. In addition a driver for the trephine may now have to be offset from the trephine longitudinal axis. Access to the patella tendon 245 therefore requires a trephine 300 having an circumferential open portion 305 or angular gap α, sized for placing around the patella tendon 245. Shown in FIG. 13B-D show an arrangement of gears for rotating the trephine 300 with an angular gap α and powering the trephine through 360° at a location that is offset from the trephine cutting tube 300 may include a driver gear 310 and two or more intermediate gears 315a and 315b to rotate the trephine 300 is therefore disclosed. The angular gap α between intermediate gears 315a and 315b should be greater than the angular gap α in the trephine 300, such that at least one of the intermediate gears 315a or 315b is engaged with trephine 300 at all rotations. The gears 310, 315a, 315b and trephine 300 may be held in a rigid housing 320 with bearings and bushings around the trephine, as schematically shown in FIG. 13D.

QT Harvest Termination

Figure 14A:
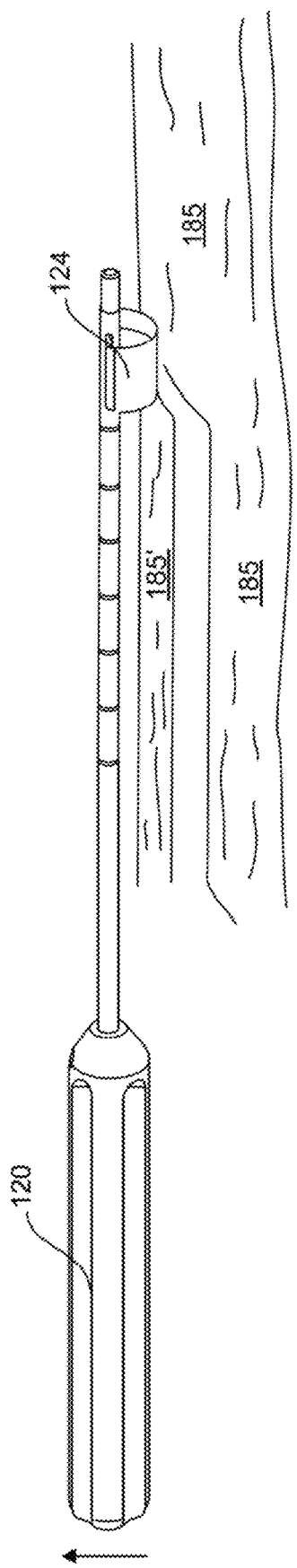
FIG. 14A schematically shows a first method of amputating a graft in accordance with at least some embodiments.
Figure 14B:
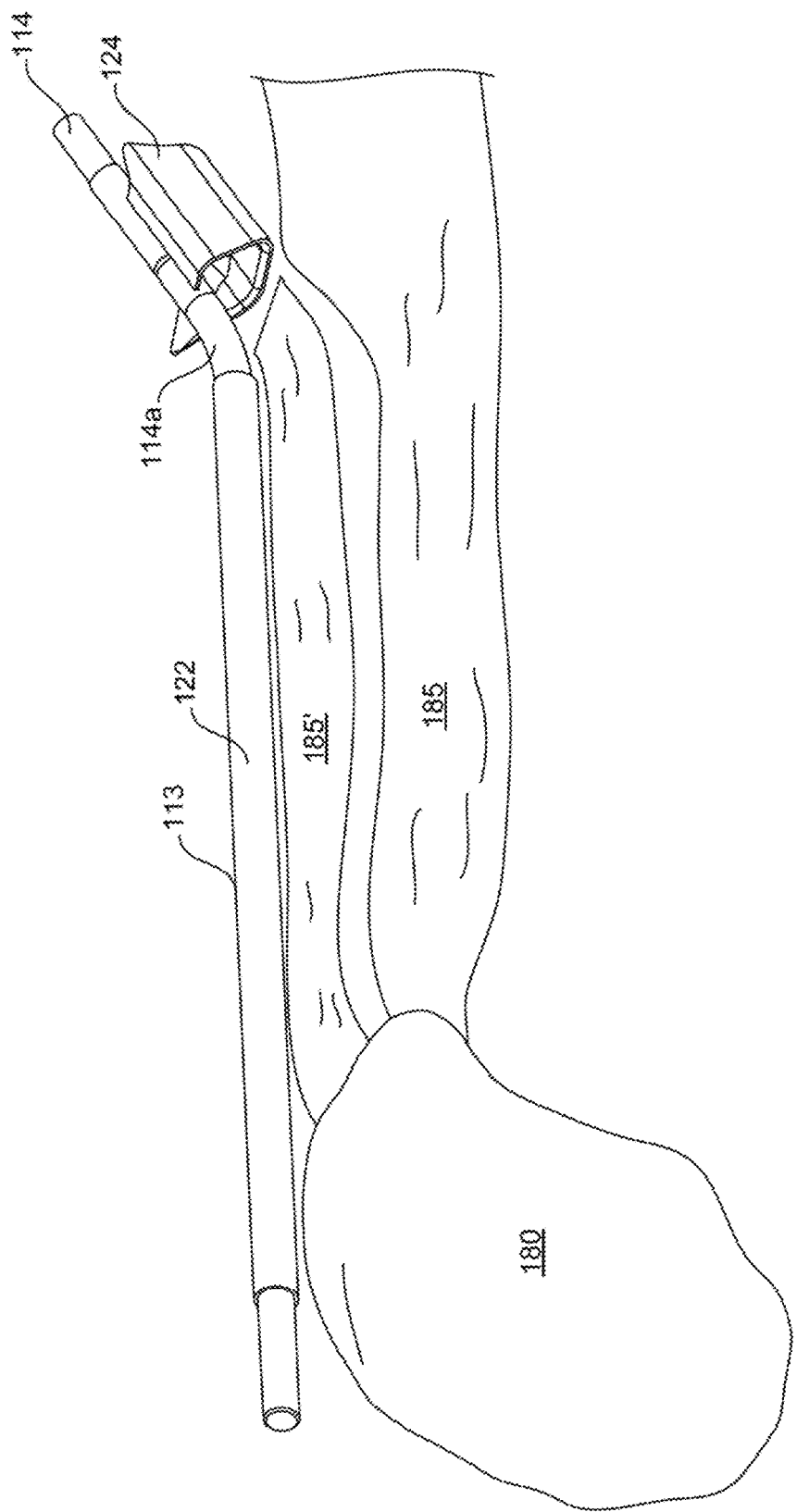
FIG. 14B schematically shows an alternative embodiment for amputating a graft using a flexible or hinged shaft in accordance with at least some embodiments.

Methods and system are also disclosed for amputating or terminating the QT 185 once the required graft length has been stripped from QT. Using harvesters 120 similar to those described in previous figures, a QT may be stripped at a consistent depth to create a graft 185' having a uniform thickness. Once a targeted length of graft has been stripped, a means of easily, quickly and reliably terminating or amputating the graft is herein described. One method of amputation using some of the harvesters embodiment described herein, may simply be elevating or lifting the cutting portion 124 of harvester anteriorly, as represented in FIG. 14A. The method may alternatively include a combination of rotation of shaft 122 while elevating the harvester 120 may also amputate the graft 185' while removing cutting portion 124 from within the QT 185. A release in the guide 100 may be configured to selectively allow rotation and or elevation of the harvester 120 so as to move the cutting portion 124 anteriorly. Alternatively cutting portion 124 may be selectively angled with respect to shaft 122 axis thus allowing anterior trajectory and graft amputation. Seen in FIG. 14B, a distal end of shaft 122 may be hinged or flexible and may be selectively angled using cables, for example. Cables (not shown) may be operatively coupled to a portion of harvester handle 120 and activation may pull cables and move cutting portion 124 to a position similar to that shown in FIG. 14B that is operable to terminate graft 185'. Alternatively shaft may include an outer tube 113 and an inner tube or shaft 114, the inner tube having a preformed curved portion 114a which may include a Nitinol tube. Inner tube 114 may be concentrically disposed within the straight outer tube 113 and also coupled to cutting portion 124 such that movement of the pre-curved tube 114 axially along outer shaft 113 may relax the preformed curved tube into the curve shape and direct the cutting portion 124 anteriorly so as to terminate the graft 185'.

Figure 14C:
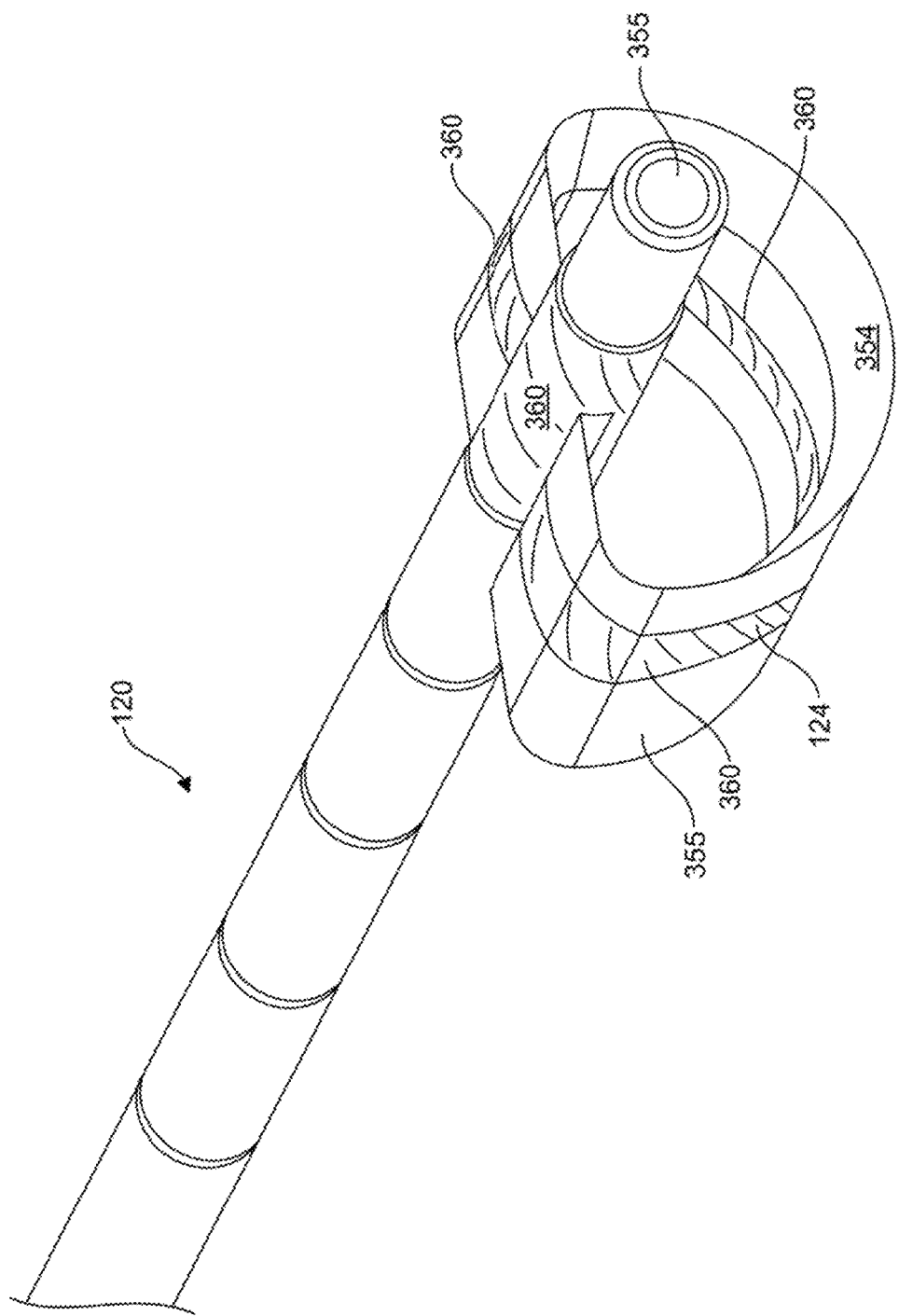
FIG. 14C schematically shows an alternative embodiment for amputating a graft using energy in accordance with at least some embodiments.

Alternatively, as shown in FIG. 14C a distal edge of cutting portion 124 may be coupled to a power supply, configured to selectively supply energy sufficient to cut or volumetrically remove tissue. An exemplary Coblation controller and system that volumetrically removes tissue using an ionized vapor may supply an electrical output to the tip of harvester 120, with the distal edge coupled as an active electrode 354 and a shaft an exemplary return electrode 355. Alternatively, the distal edge 125 of cutting portion may act as the active electrode 354, while a proximal portion of cutting portion may act as the return electrode 355. An electrical insulator 360 is shown between the electrodes to direct the energy through the tissue 185. Rotation of the cutting portion 124 back to the first, upward facing position along with a concomitant supply of energy may aid in graft amputation. A more detailed description of the phenomena and electrode configurations can be found in commonly assigned U.S. Pat. No. 5,697,884, the complete disclosure of which is incorporated herein by reference.

Figure 14D:
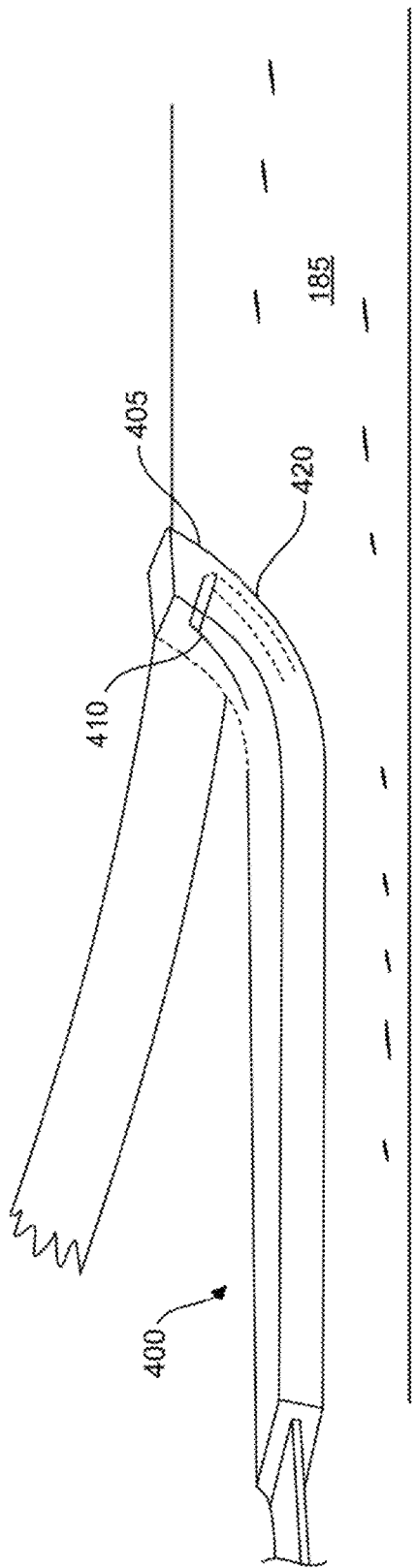
FIG. 14D schematically shows an alternative embodiment for amputating a graft using device with a cutting block in accordance with at least some embodiments.
Figure 14E:
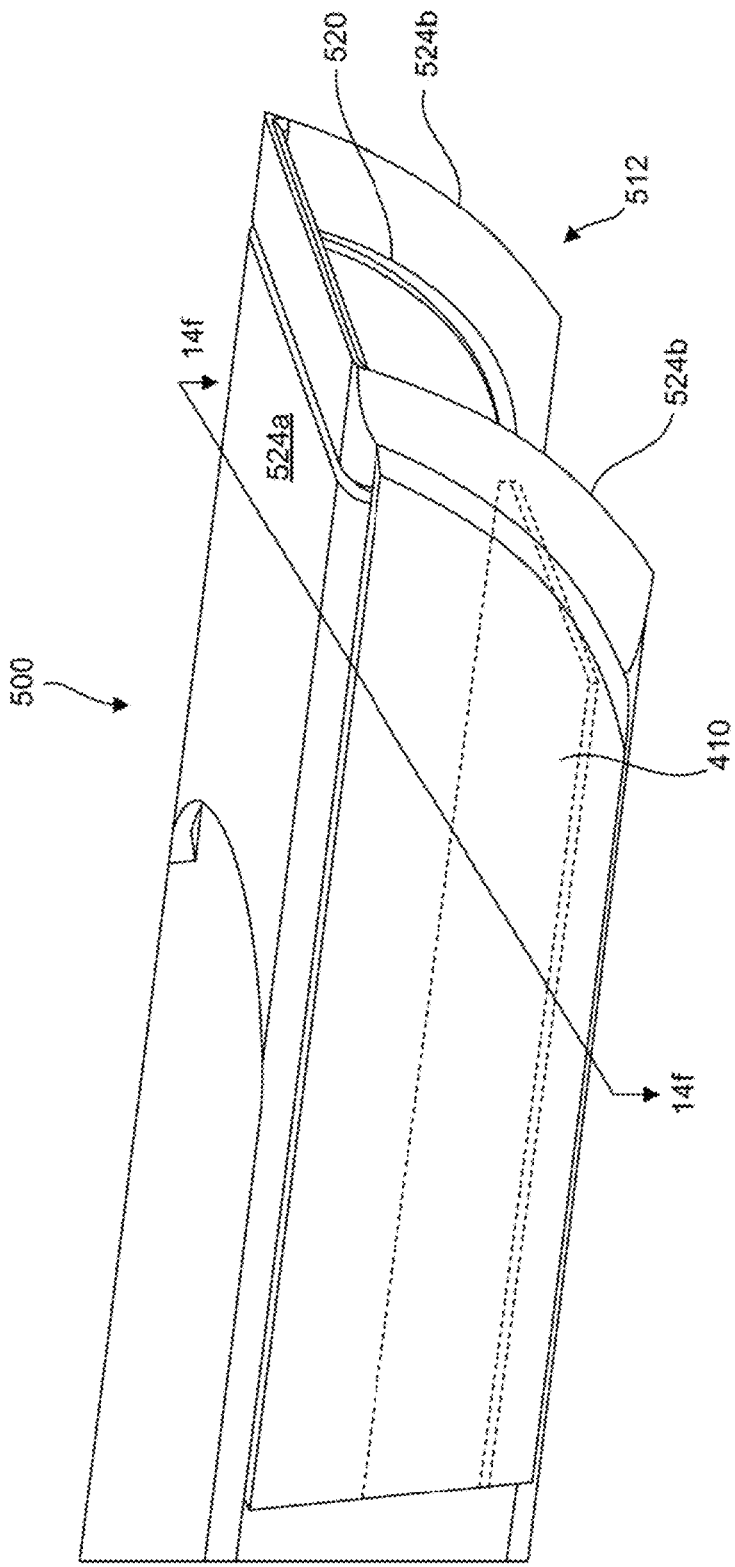
FIGS. 14E-14F schematically show an isometric and cross section view respectively of a combination harvesting and amputating instrument of an alternative embodiment for amputating a graft, in a retracted configuration.
Figure 14F:
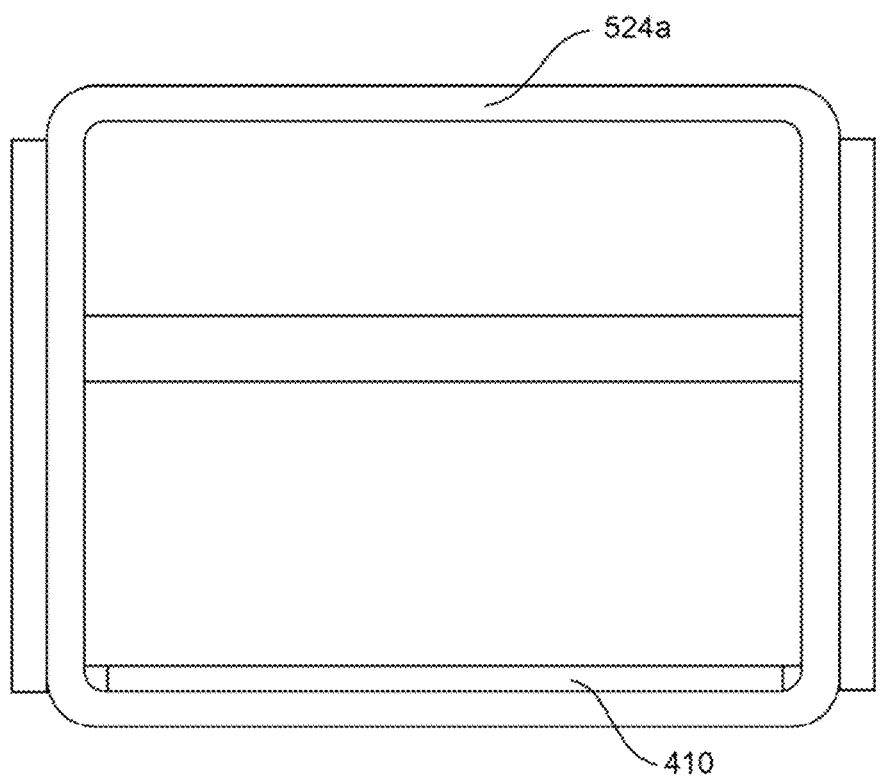
Figure 14G:
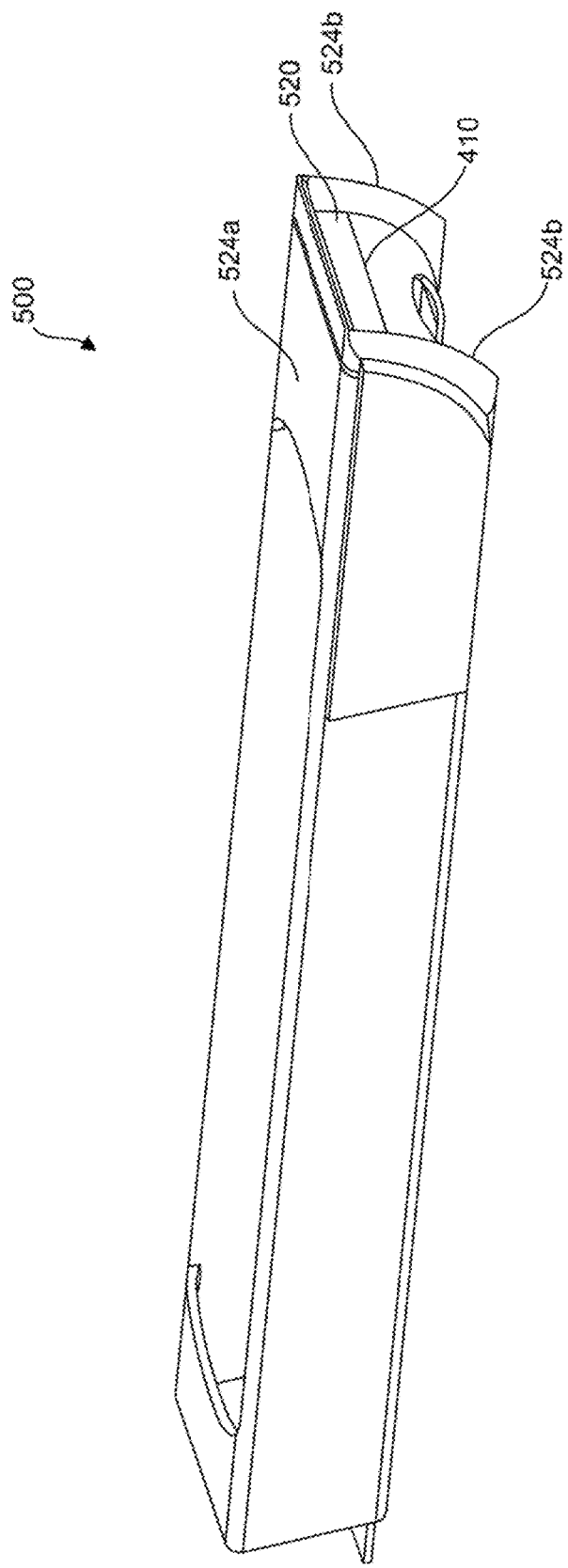
FIGS. 14G-14H schematically show an isometric and cross section view respectively of a combination harvesting and amputating instrument of the embodiment in FIGS. 14E and 14F, with the cutting block advanced.
Figure 14H:
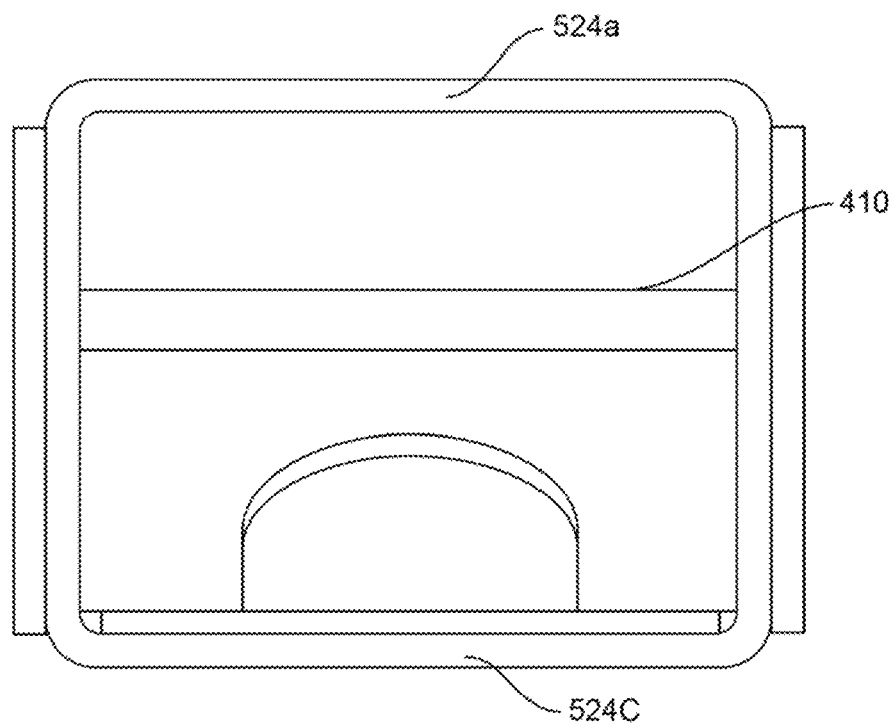

A further embodiment shown in FIG. 14D may include a separate amputating tool 400, with a distally disposed angled portion 405. Cutting tool 400 may be configured to slide underneath the prepared strip of QT 185 and may generally be rectangular in cross section, so as to easily slide into and along the QT. Amputating tool 400 may include a blade portion 410, having a width sufficient to terminate the entire width of QT graft and therefore cutting blade portion 410 may have a width equivalent to a corresponding cutting portion 124 of harvester 120. Blade portion 410 may be axially slideable so as to selectively emerge from a shaft 420 at the desired location. Blade portion 410 may slide along an internal lumen of shaft 420 so as to emerge from a cavity at the distal end of shaft. Blade 410 may be flexible so as to easily curve around and extend from angled portion 405. Amputating tool 400 may be configured to fit within an opening 115 of guide 100, or through an alternative portion of guide 100.

A further embodiment represented in end view FIG. 14E-H shows a combination harvester 500 with amputation similar to the tool 400. Cutting portion 524 may include a surfboard 524a and at least one lateral cutting leading edges 524b (two shown). A leading edge of moveable cutting block 410 may be disposed at opening to cutting portion so as to aid in forming a posterior surface of graft. In other embodiments cutting block 410 may be more retracted and a cutting edge may be disposed along the posterior edge 524c. With the cutting bock retracted 410, the length of graft strip may be initially formed and once termination of graft is desired, cutting block 410 may be advanced along tracks 520 of open distal end 512 of harvester 500. The cutting block (or blade 410) may also have a pre-formed curved shape configured to curve anteriorly towards anterior surface of graft so as to terminate graft. Cutting blade may be a Nitinol material to relax into preformed curve once released from harvester distal end 512.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A tendon harvesting system for forming a tendon graft from a native tendon comprising:
   a guide and a harvesting instrument, the guide defining an elongate body with a first end and a tapered second end, the tapered second end configured to extend subcutaneously and along a longitudinal axis of the native tendon, the guide also including;
   an opening configured to receive the harvesting instrument therethrough and guide access to the native tendon;
   wherein the harvesting instrument includes a shaft and a cutting portion, and the guide and the harvesting instrument are configured to cooperate and define a trajectory of the harvesting instrument along the native tendon longitudinal axis, the trajectory defining a first direction, and also define a depth of cut with the cutting portion into the native tendon, the depth of cut extending in a second direction angularly offset from the first direction and thereby form a uniform tendon graft thickness.

2. The tendon harvesting system of claim 1 wherein the guide includes a handle extending from the first end and configured to place the guide subcutaneously.

3. The tendon harvesting system of claim 1 wherein the opening defines a non-circular shape.

4. The tendon harvesting system of claim 1 wherein the guide is shaped in a "C" or "U".

5. The tendon harvesting system of claim 1 wherein the guide is configured to retract a tissue that is adjacent the native tendon.

6. The tendon harvesting system of claim 1 wherein the guide is configured to flex.

7. The tendon harvesting system of claim 1 wherein the guide is a unibody.

8. The tendon harvesting system of claim 1 further comprising a transecting means, wherein the guide is configured to place the transecting means at the tapered end, to selectively transect an end of the tendon graft from the native tendon.

9. The tendon harvesting system of claim 1 wherein the harvesting instrument comprises two parallel blades, configured to form two lateral sides of the tendon graft simultaneously.

10. The tendon harvesting system of claim 9, wherein the harvesting instrument comprises a surfing surface configured to surf an anterior surface of the native tendon, as the two parallel blades extend along and into the native tendon.

11. The tendon harvesting system of claim 1 wherein the harvesting instrument is configured to slide along the native tendon with the shaft sliding above the native tendon, while the cutting portion extends into and cuts along the native tendon.

12. A tendon harvesting system for forming a tendon graft from a native tendon comprising:
- a harvesting instrument having a shaft and a blade, the shaft defining a longitudinal axis, and the blade extending at an angular offset away from the longitudinal axis; and
- a guide defining an elongate body with a first end and a tapered second end including;
- a reference surface extending between the first end and the tapered second end, configured to extend subcutaneously along a longitudinal axis of the native tendon; and
- an opening through the guide configured to receive the blade of the harvesting instrument therethrough to guide access of the blade to the native tendon; wherein the guide and the harvesting instrument are configured to cooperate and define both a pathway of the harvesting instrument along the native tendon and a depth of cut of the blade into the native tendon to form a uniform tendon graft thickness.

13. The tendon harvesting system of claim 12 further comprising a handle extending from the first end and configured to place the guide subcutaneously.

14. The tendon harvesting system of claim 12 wherein the opening defines a non-circular shape.

15. The tendon harvesting system of claim 12 wherein the guide is shaped in a "C" or "U".

16. The tendon harvesting system of claim 12 wherein the guide is a flexible unibody.

17. The tendon harvesting system of claim 12 further comprising a truncating blade, and wherein the opening is also configured to guide a location of the truncating blade towards the tapered end to selectively terminate an end of the tendon graft from the native tendon.

18. The tendon harvesting system of claim 12 wherein the harvesting instrument comprises two parallel blades disposed at the end of the shaft and away from the shaft longitudinal axis, configured to form two lateral sides of the tendon graft simultaneously.

19. The tendon harvesting system of claim 18 wherein the harvesting instrument comprises a surfing surface configured to surf an anterior surface of the native tendon, as the two parallel blades extend along and into the native tendon.

20. The tendon harvesting system of claim 12 wherein the harvesting instrument is configured to be inserted through the guide opening to place the blade on an exterior surface of the native tendon and then rotate the harvesting instrument to place the blade into the native tendon.

* * * * *